(12) United States Patent
Zhao et al.

(10) Patent No.: US 7,479,377 B2
(45) Date of Patent: *Jan. 20, 2009

(54) GENETIC CONSTRUCT INTRACELLULAR MONITORING SYSTEM

(75) Inventors: Sharon Zhao, Union City, CA (US); Inna Vainshtein, Palo Alto, CA (US); Richard M. Eglen, Los Altos, CA (US)

(73) Assignee: DiscoveRx Corporation, Fremont, CA (US)

( * ) Notice: Subject to any disclaimer, the term of this patent is extended or adjusted under 35 U.S.C. 154(b) by 401 days.

This patent is subject to a terminal disclaimer.

(21) Appl. No.: 10/229,747

(22) Filed: Aug. 27, 2002

(65) Prior Publication Data

US 2003/0092070 A1    May 15, 2003

Related U.S. Application Data

(60) Provisional application No. 60/316,428, filed on Aug. 30, 2001, provisional application No. 60/343,156, filed on Oct. 21, 2001, provisional application No. 60/353,086, filed on Jan. 30, 2002.

(51) Int. Cl.
| | |
|---|---|
| *G12Q 1/68* | (2006.01) |
| *G01N 33/53* | (2006.01) |
| *G01N 33/58* | (2006.01) |
| *C12N 15/00* | (2006.01) |
| *C12N 5/10* | (2006.01) |
| *C12N 5/16* | (2006.01) |

(52) U.S. Cl. .......................... 435/7.6; 435/6; 435/7.21; 435/320.1; 435/325

(58) Field of Classification Search .................. 435/6, 435/7.1, 69.1, 320.1, 325; 536/23.1, 23.4
See application file for complete search history.

(56) References Cited

FOREIGN PATENT DOCUMENTS

| EP | 0551842 A2 | 10/1985 | .................... 15/70 |
|---|---|---|---|
| WO | WO 9954732 | 10/1999 | .................... 33/53 |

OTHER PUBLICATIONS

Rossi et al, Monitoring protein-protein interactions in intact eukaryotic cells by -galactosidase complementation, PNAS, Aug. 1997, vol. 94, pp. 8405-8410.*
Mohler and Blau, Gene expression and cell fusion analyzed by lacZ complementation in mammalian cells, PNAS, Oct. 1996, vol. 93, pp. 12423-12427.*
Moosman and Rusconi, Alpha complementation of LacZ in mammalian cells, NAR, 1996, vol. 24, No. 6, pp. 1171-1172.*
C. G. Copley, et al., BioFeedback, Exonuclease Cycling Assay: An Amplified Assay for the Detection of Specific DNA Sequences, *BioTechniques*, 13/6:888-892 (1992).
Daniel R. Henderson, et al., CEDIA™, A New Homogeneous Immunoassay System, *Clinical Chemistry*, 32/9:1637-1641 (1986).

\* cited by examiner

*Primary Examiner*—Maria B Marvich

(57) ABSTRACT

A system is provided an enzyme donor ("ED") fused a surrogate of a mammalian protein of interest, where the fusion protein has the function of the natural protein. A vector is provided comprising a regulatory region functional in a mammalian host cell, a sequence encoding the ED joined to a multiple cloning site, an enzyme acceptor ("EA") protein or enzyme acceptor sequence encoding such protein, and substrate for the enzyme formed by ED and EA.

10 Claims, 17 Drawing Sheets

```
5'ATG AGC TCC AAT TCA CTG GCC GTC GTT TTA CAA CGT CGT GAC TGG GAA AAC CCT
   Met Ser Ser Asn Ser Leu Ala Val Val Leu Gln Arg Arg Asp Trp Glu Asn Pro

GGC GTT ACC CAA CTT AAT CGC CTT GCA GCA CAT CCC CCT TTC GCC AGC TGG CGT
Gly Val Thr Gln Leu Asn Arg Leu Ala Ala His Pro Pro Phe Ala Ser Trp Arg

AAT AGC GAA GAG GCC CGC ACC GAT CGC CCT TCC CAA CAG TTG CGC AGC CTG AAT
Asn Ser Glu Glu Ala Arg Thr Asp Arg Pro Ser Gln Gln Leu Arg Ser Leu Asn

GGC GAA TAG  3'
Gly Glu ***
```

Figure 1: Enzyme Donor Amino Acid and Nucleic Acid Sequences

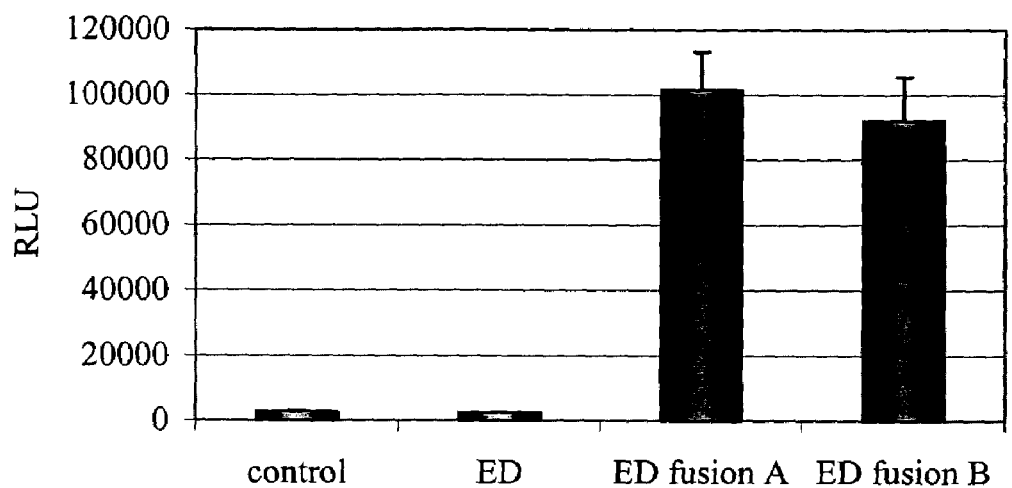
Figure 2: ED Activity in Cells - Fused and Unfused

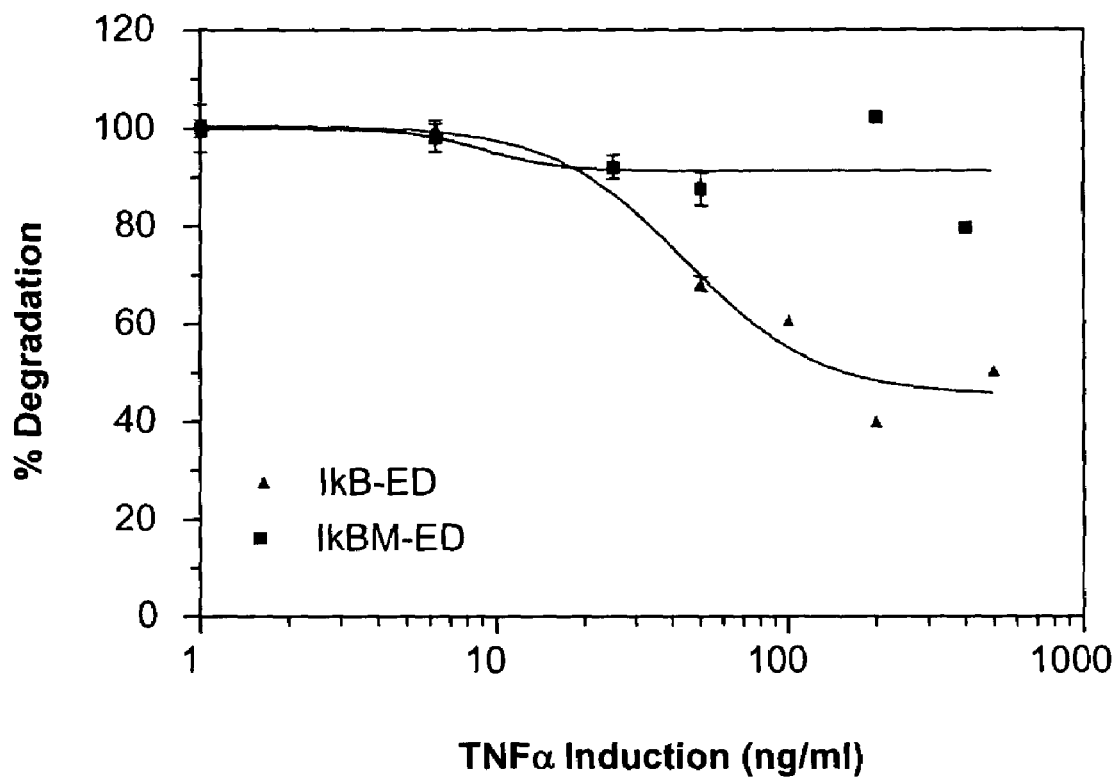
Figure 3: TNF-Induced IkB Degradation in HeLa Cells

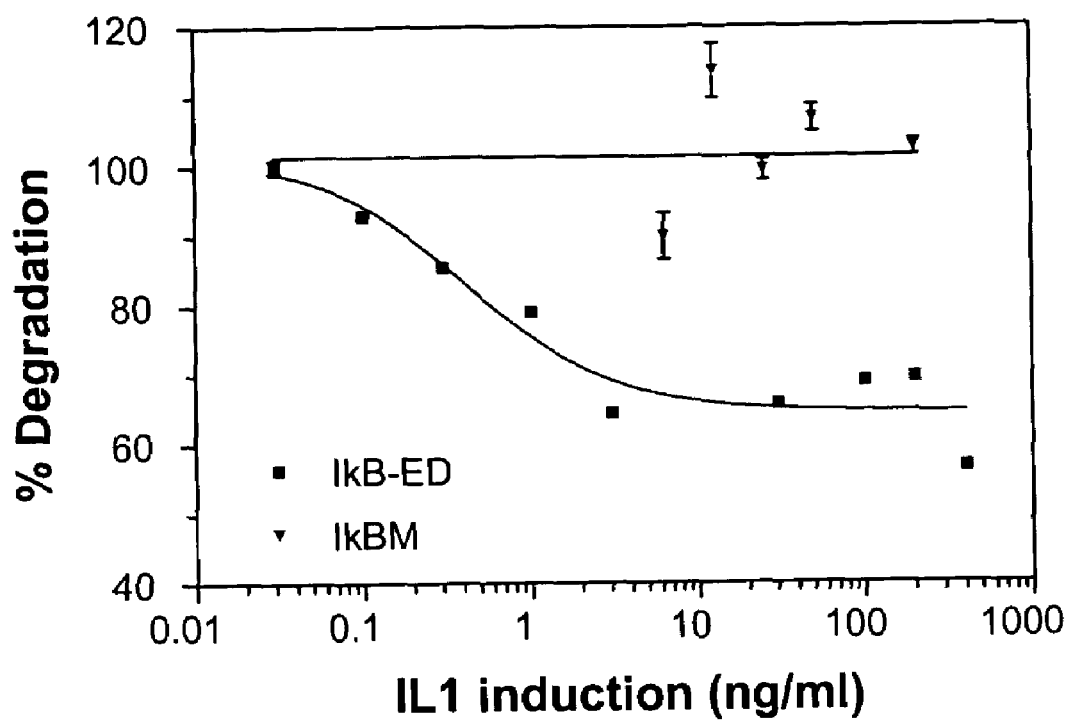
Figure 4. IL1-Induced IkB-ED Degradation in HeLa Cells

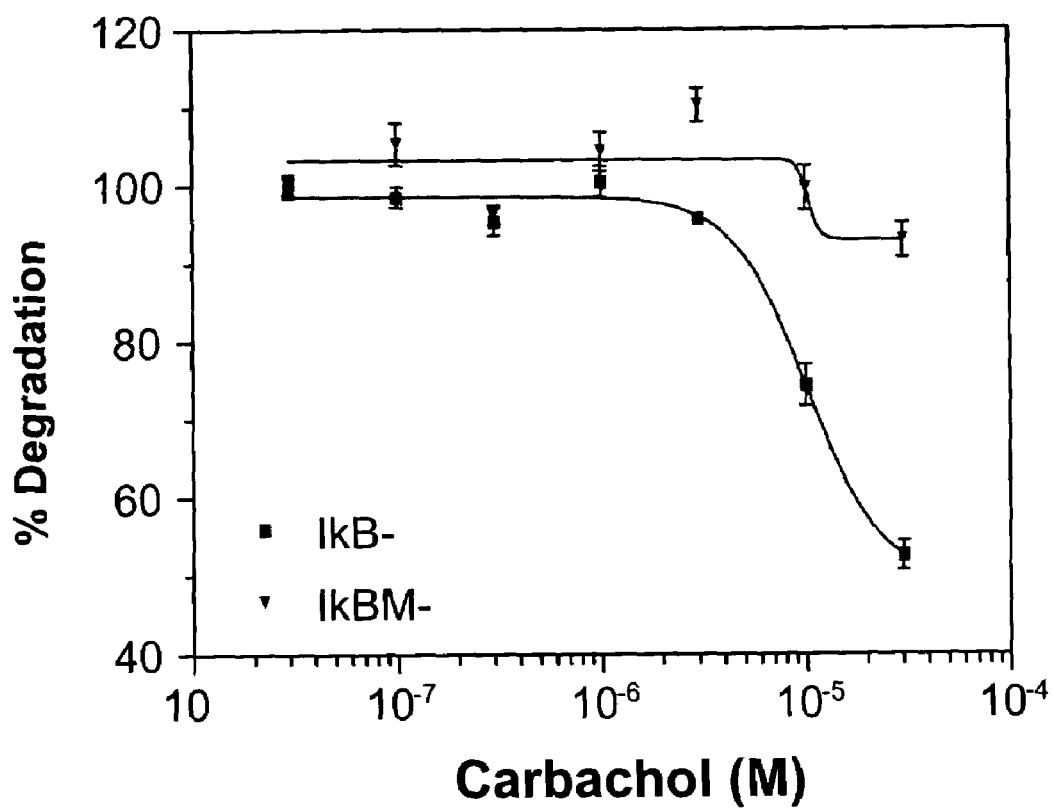
Figure 5. Carbachol-Induced IkB-ED Degradation in SK-N-SH Cells

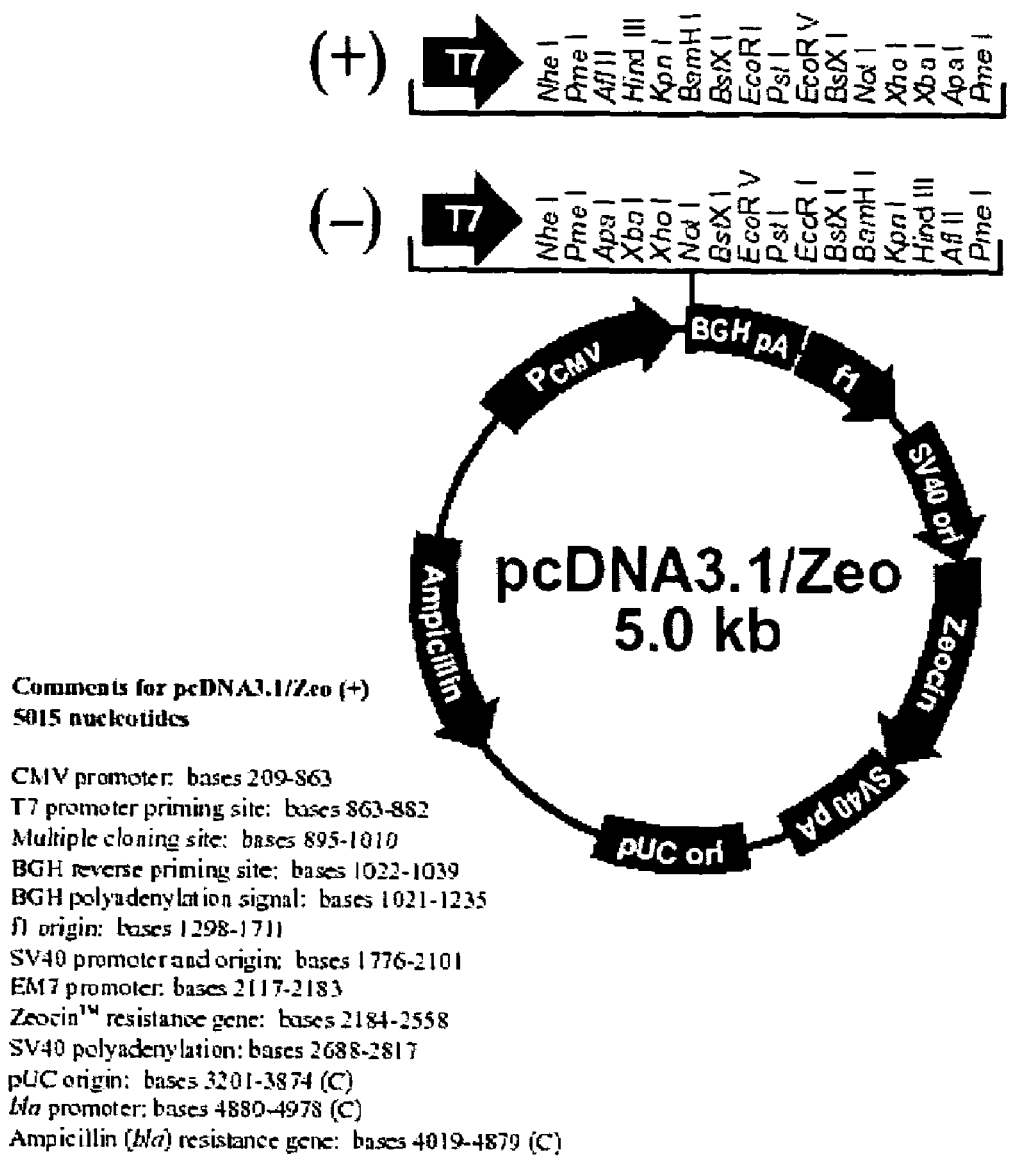
Figure 6. pcDNA3.1/zeo vector (Invitrogen)

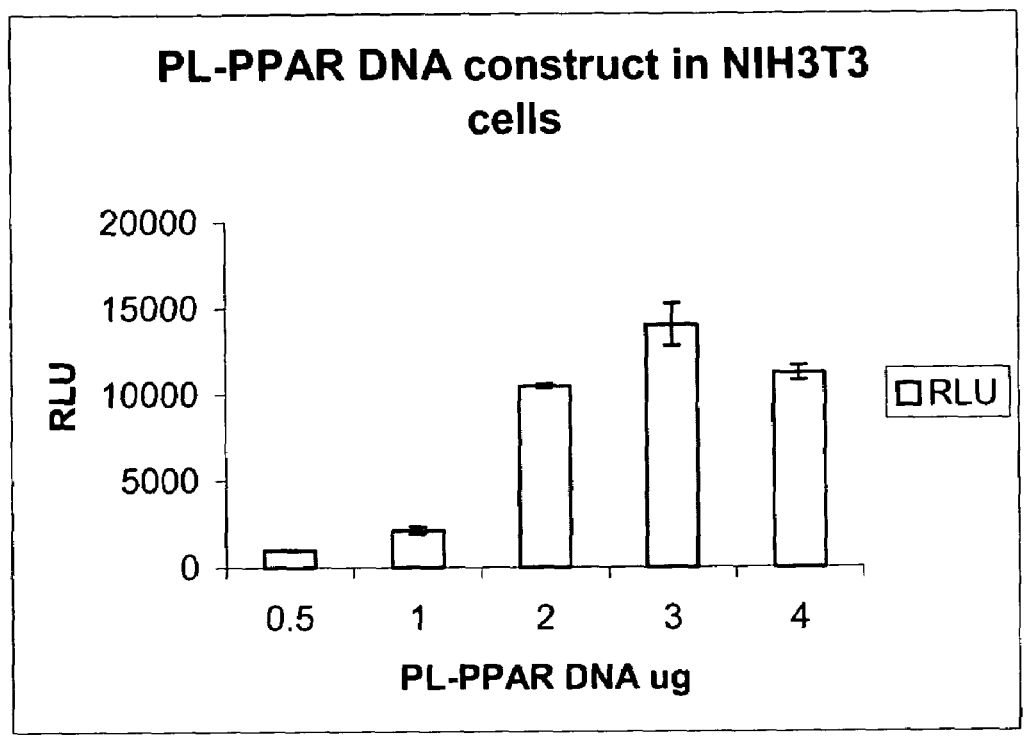
Figure 8. EFC Activity Readouts vs PL-PPAR Construct

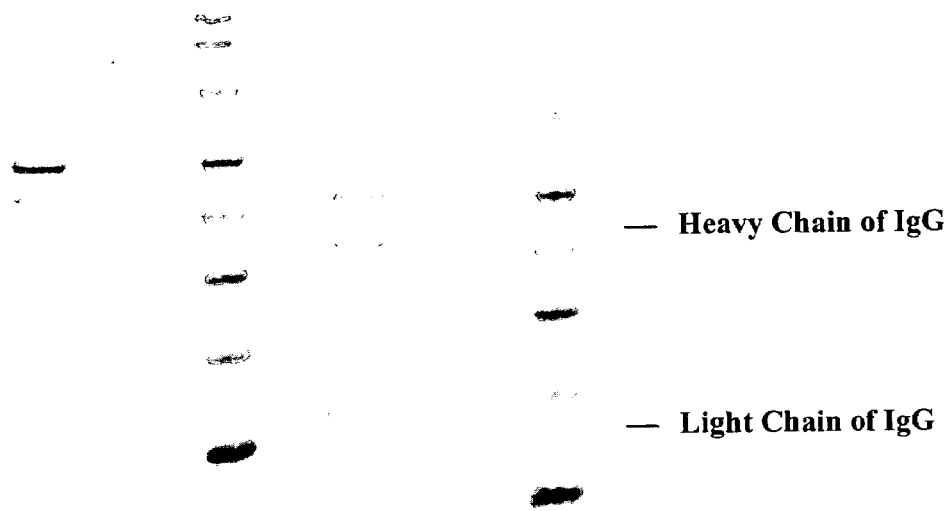
Figure 9. Western Blot of Total Cell Lysates and Immunoprecipitates of PL-PPAR Transiently Expressed in HEK-293 cells. Arrow shows PL-PPAR Construct.

FIG. 13A
DMSO CTZ
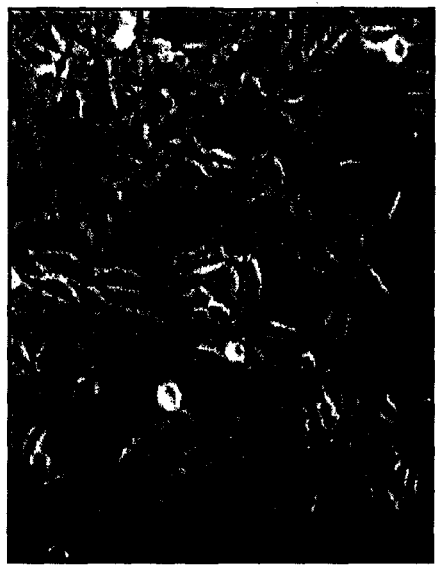 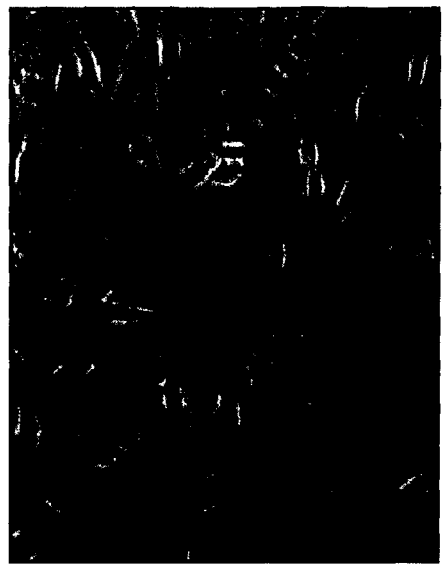
NIH3T3 Cells
DMSO CTZ
 
ECV304 Cells
FIG. 13B

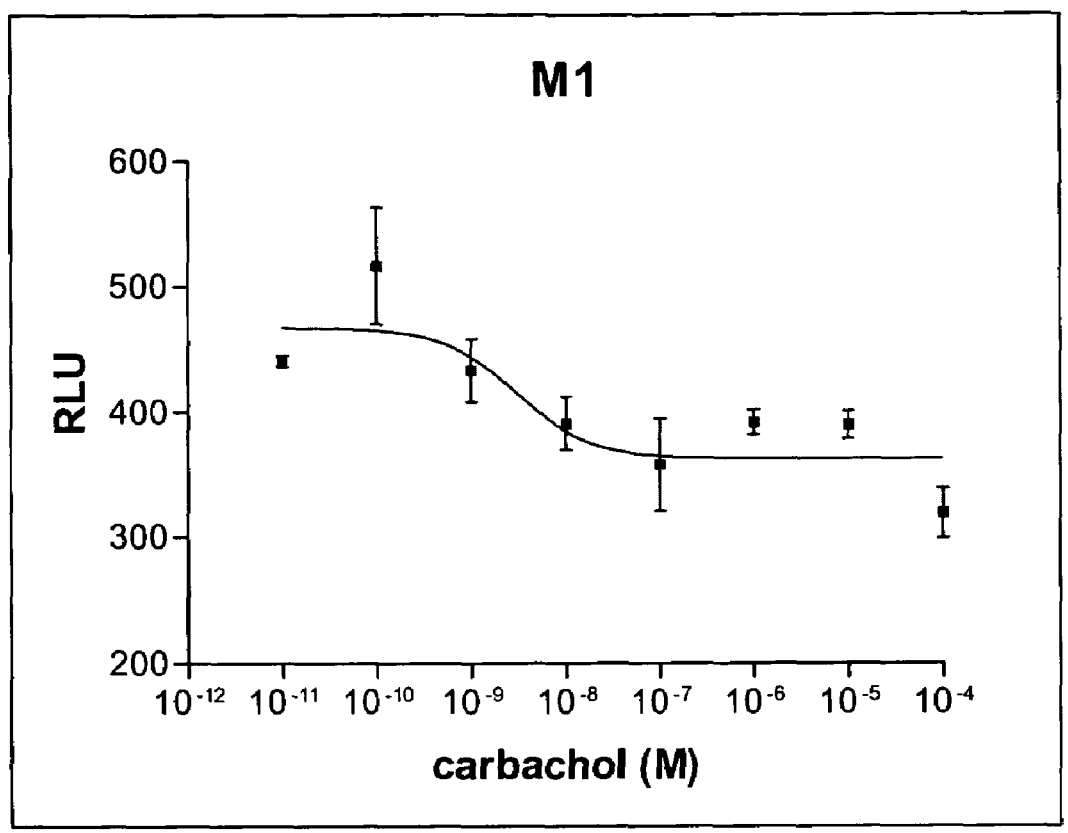
Figure 14. M1 Activation in CHO-K1 cells

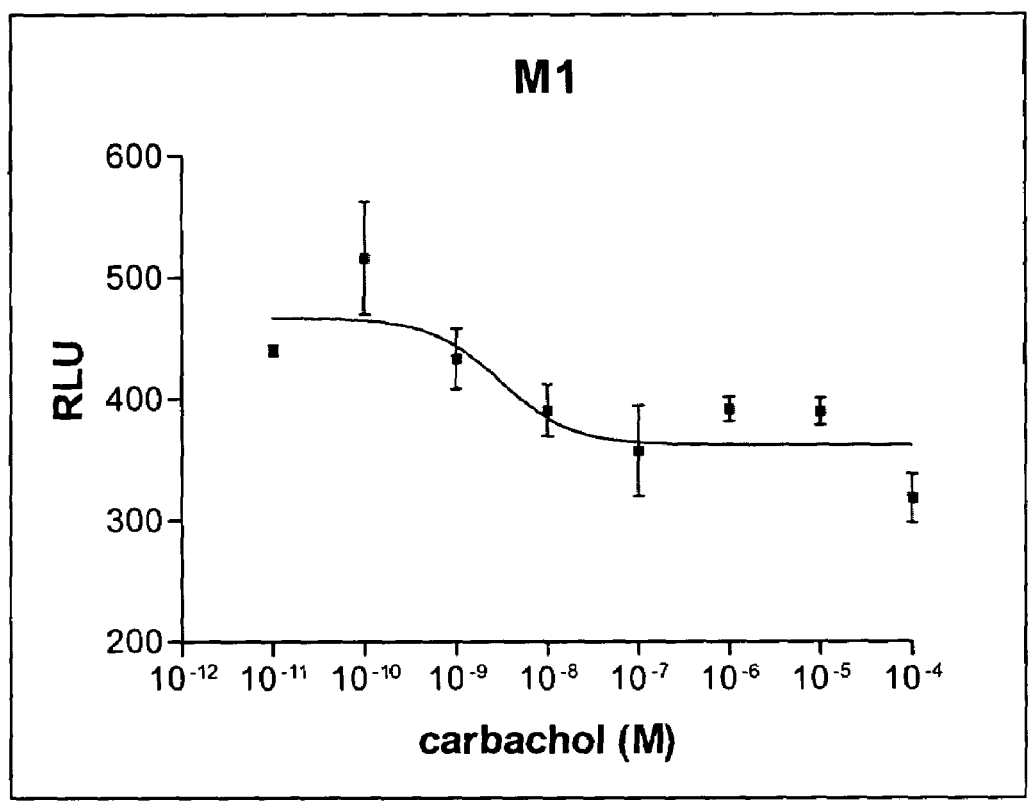
Figure 15. MC4 Activation in CHO-K1 Cells

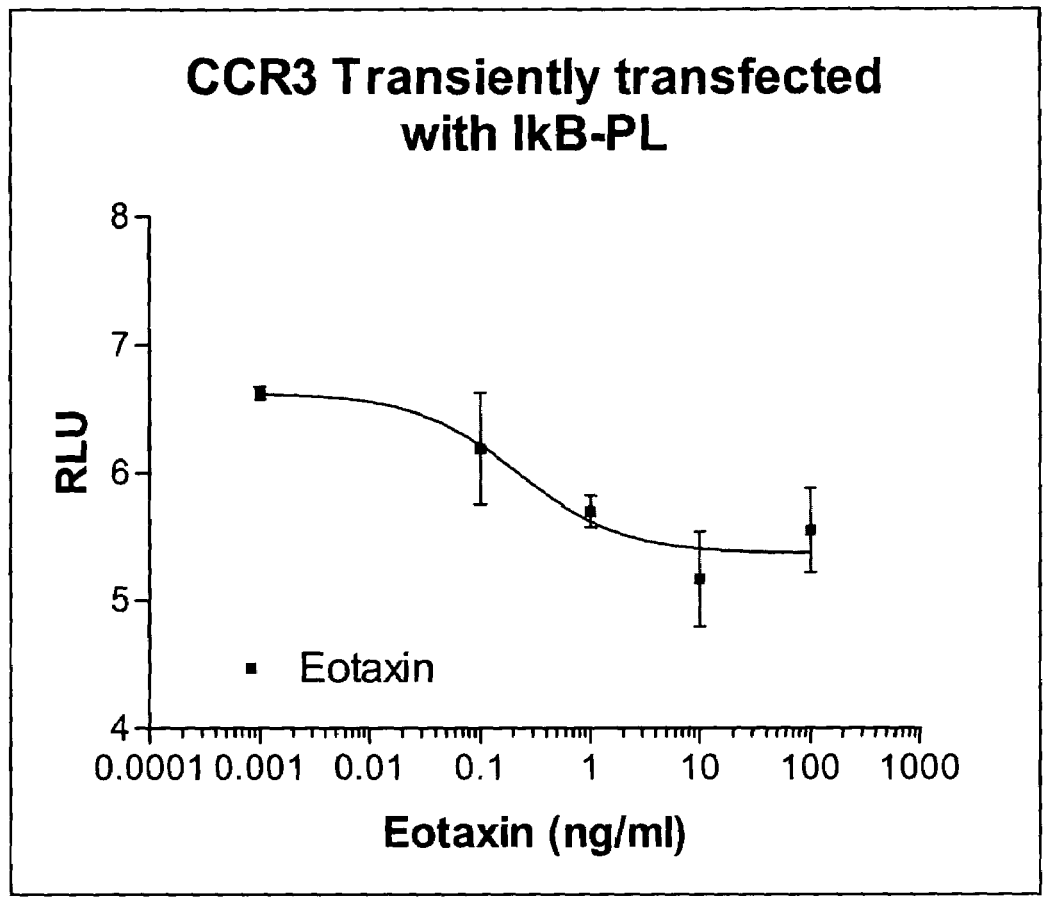
Figure 16. CCR3 Activation in CHO-K1 Cells

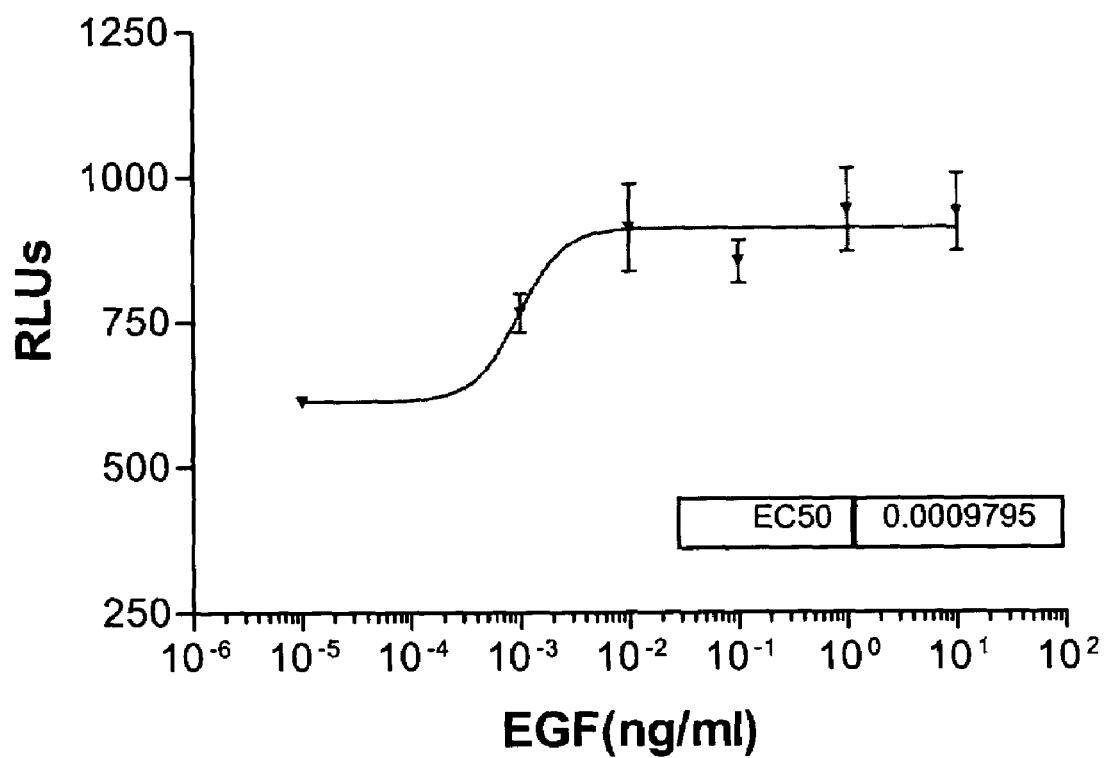
Figure 17. EGFR Activation for Cell Viability

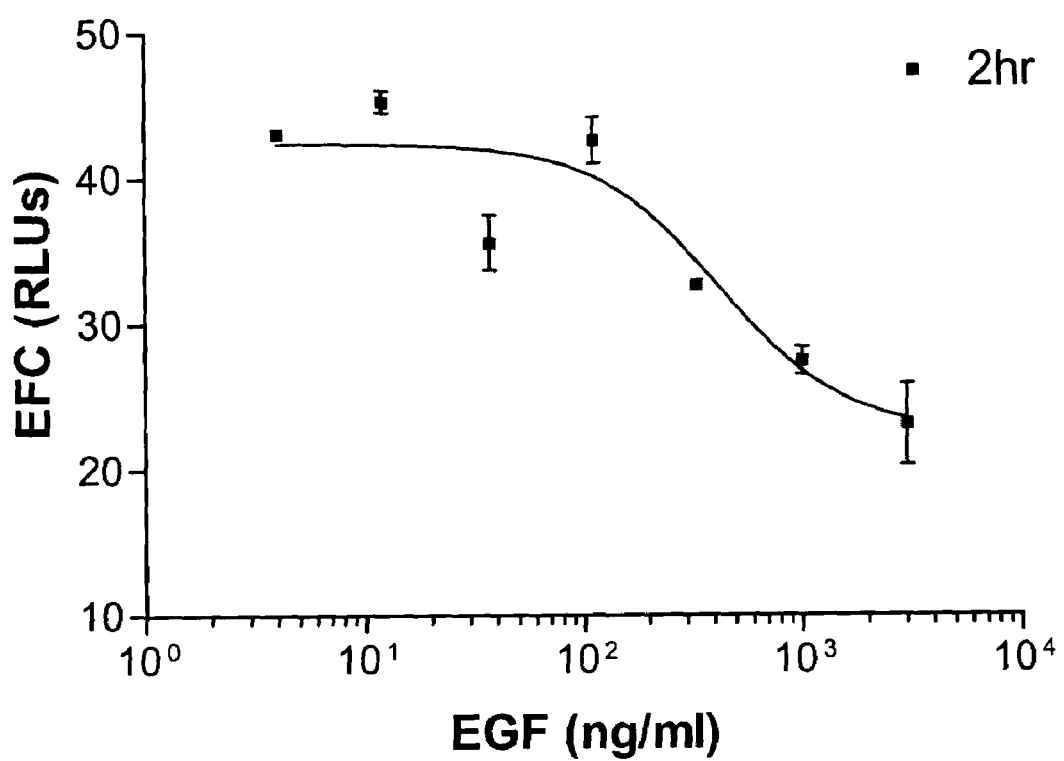
Figure 18. IkB Degradation upon EGF Activation in HeLa Cells

SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 1
ccgaagctta tgttccaggc ggccgag                                    27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 2
ataggatcct aacgtcagac gctggcc                                    27

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 3
ataggatcca tgagctccaa ttcactggcc g                               31

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 4
ataagaatgc ggccgcctat tcgccattca ggctgcgc                        38

-continued

```
<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 5
agacggtacc atgaccatgg ttgacacaga gatg                              34

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 6
gtcctctaga tgttcctgaa catgatccgc cggcgcaga                         39

<210> SEQ ID NO 7
<211> LENGTH: 171
<212> TYPE: DNA
<213> ORGANISM: Unknown Organism
<220> FEATURE:
<223> OTHER INFORMATION: Description of Unknown Organism: Enzyme donor
      nucleotide sequence
<220> FEATURE:
<221> NAME/KEY: CDS
<222> LOCATION: (1)..(168)

<400> SEQUENCE: 7 atg agc tcc aat tca ctg gcc gtc gtt tta caa cgt cgt gac tgg gaa    48
Met Ser Ser Asn Ser Leu Ala Val Val Leu Gln Arg Arg Asp Trp Glu
 1               5                  10                  15 aac cct ggc gtt acc caa ctt aat cgc ctt gca gca cat ccc cct ttc    96
Asn Pro Gly Val Thr Gln Leu Asn Arg Leu Ala Ala His Pro Pro Phe
                20                  25                  30 gcc agc tgg cgt aat agc gaa gag gcc cgc acc gat cgc cct tcc caa   144
Ala Ser Trp Arg Asn Ser Glu Glu Ala Arg Thr Asp Arg Pro Ser Gln
            35                  40                  45 cag ttg cgc agc ctg aat ggc gaa tag                               171
Gln Leu Arg Ser Leu Asn Gly Glu
        50                  55

<210> SEQ ID NO 8
<211> LENGTH: 56
<212> TYPE: PRT
<213> ORGANISM: Unknown Organism
<220> FEATURE:
<223> OTHER INFORMATION: Description of Unknown Organism: Enzyme donor
      amino acid sequence

<400> SEQUENCE: 8

Met Ser Ser Asn Ser Leu Ala Val Val Leu Gln Arg Arg Asp Trp Glu
 1               5                  10                  15

Asn Pro Gly Val Thr Gln Leu Asn Arg Leu Ala Ala His Pro Pro Phe
                20                  25                  30

Ala Ser Trp Arg Asn Ser Glu Glu Ala Arg Thr Asp Arg Pro Ser Gln
            35                  40                  45

Gln Leu Arg Ser Leu Asn Gly Glu
        50                  55
```

GENETIC CONSTRUCT INTRACELLULAR MONITORING SYSTEM

This application is a continuation-in-part of companion provisional applications Ser. No. 60/316,428, filed Aug. 30, 2001, Ser. No. 60/343,156, filed Oct. 21, 2001 and Ser. No. 60/353,086, filed Jan. 30, 2002, the entire contents of which are incorporated herein by reference.

BACKGROUND OF THE INVENTION

1. Field of the Invention

The invention relates generally to the cellular monitoring of protein expression and processing.

2. Background Information

The elucidation of the human genome and that of other species has greatly accelerated with the interest in proteomics, that is, the study of naturally occurring proteins and their intra- and extracellular interactions and activities. The ability to determine the status of a protein in a cell has far ranging opportunities in understanding the intracellular pathways, the intracellular movement of proteins into different compartments, the regulation of transcription and expression, the regulation of protein content and protein modification, and the like. Not only will this provide greater insight into how a cell operates, but it also allows for the determination of when a cell is aberrant or diseased. In addition, one can determine the effect of changes in the environment of the cell on the cellular function, as evidenced by changes in protein profiles, modification of proteins and transport of proteins.

Various approaches have been used to study protein-protein interactions, particularly using yeast as a host. While this can provide information concerning whether two proteins will interact, it gives no information about what happens in a native cell. The use of yeast as a host may also provide information about compounds that interfere with the interaction, but in an environment substantially different from the mammalian natural environment where the interaction may occur.

Other techniques have involved tagging a protein with a peptide fluorescer, e.g., green fluorescent protein, where degradation of the fusion protein can be followed by the loss of the fluorescence. This has many disadvantages in requiring a very large tag that may interfere with the folding of the native protein, its binding to other proteins, its susceptibility to degradation and its overall regulatory activity.

In studying the effect of drugs, both as to efficacy and differences in individual responses, it would be helpful to understand the differences in the individual hosts that result in the different responses. In understanding diseased states, it would be advantageous to be able to compare the changes in protein activity as a result of the cellular diseased state. By providing the capability to monitor changes in one or more proteins, therapeutic, diagnostic and scientific information can be developed.

BRIEF DESCRIPTION OF RELEVANT LITERATURE

U.S. Pat. No. 6,037,133 describes the use of green fluorescent protein fusion with IκB for measuring IκB degradation. See also, Li, et al., *J. Biol. Chem.*, 1999, 274:21244-50. Douglas, et al., *Proc. Natl. Acad. Sci. USA*, 1984, 81:3983-7 describes the fusion protein of ATP-2 and lacZ. WO92/03559 describes a fusion protein employing β-complementation of β-galactosidase for measuring proteinases. WO01/0214 describes protein folding and/or solubility assessed by structural complementation using the α-peptide of β-galactosidase as a fusion protein. WO01/60840 describes fusion proteins including a fusion protein comprising an enzyme donor β-galactosidase for measuring protein folding and solubility. Homma, et al., *Biochem. Biophys. Res. Commun.*, 1995, 215, 452-8 describes the effect of β-fragments of β-galactosidase on the stability of fusion proteins. Abbas-Terki, et al., *Eur. J. Biochem.* 1999, 266, 517-23 describes α-complemented β-galactosidase as an in vivo model susbtrate for the molecular chaperone heat-shock protein in yeast. Miller, et al., *Gene*, 1984, 29, 247-50 describe a quantitative β-galactosidase α-complementation assay for fusion proteins containing human insulin β-chain peptides. Thomas and Kunkel, *Proc. Natl. Acad. Sci. USA*, 1993, 90, 7744-8 describe an ED containing plasmid to measure mutation rate.

SUMMARY OF THE INVENTION

Systems, methods and compositions are provided for intracellularly monitoring an enzyme small fragment containing fusion protein as surrogate of a protein(s) of interest as to its interactions, status and activity. The system comprises (1) a genetic construct having a transcriptional regulatory region functional in mammalian cells, a sequence encoding an enzyme donor fragment functional when complexed with an enzyme acceptor fragment to act on a substrate to produce a detectable product, the enzyme donor encoding nucleic acid functionally joined to a polylinker or multiple cloning site and optionally followed by a polyadenylation coding sequence and a transcriptional termination site; (2) the large enzyme donor fragment or an expression construct encoding the large enzyme donor fragment; optionally cells specifically modified for use with vectors comprising the genetic constructs; and (4) a substrate for the functional enzyme (holoenzyme) that provides a detectable signal. The subcomponents of the system include genetic constructs, phenotypically modified cells and assays employing the phenotypically modified cells.

The compositions comprise a fusion protein comprising the small fragment as an enzyme donor oligopeptide fused to a surrogate protein that may include the protein(s) of interest in whole or part. In the presence of the larger enzyme fragment, enzyme acceptor, active enzyme can be determined as a measure of the activity, expression level and/or amount of the protein of interest. The measurement may be intracellular by having the enzyme acceptor expressed in the cell with substrate present or a lysate may be used. Degradation, binding events, translocation and modification of the protein of interest may be determined by the assay. The enzyme fragments are characterized by providing low independent background in the presence of substrate, capable of complexing to form an active enzyme independent of other entities to hold the fragments in juxtaposition, and allowing for binding of the enzyme acceptor to the enzyme donor as the fusion product.

BRIEF DESCRIPTION OF THE DRAWINGS

FIG. 1 is the enzyme donor amino acid sequence SEQ ID NO:5 and nucleic acid sequence SEQ ID NO:6;

FIG. 2 is a graph of the ED activity in cells unfused and fused;

FIG. 3 is a graph of TNF induced IκB-ED degradation in HeLa Cells;

FIG. 4 is a graph of IL-1 induced IκB-ED degradation in HeLa Cells;

FIG. 5 is a graph of carbachol induced IκB-ED degradation in SK-N-SH cells;

FIG. 6 is a diagram of the pcDNA3.1/zeo vector;

FIG. 8 is a bar graph of the enzyme fragment complementation (β-galactosidase ED and EA complementation) activity readouts showing proportionality to the amount of the PL-PPAR construct added;

FIG. 9 shows Western blots of total cell lysates and immunoprecipitates of PL-PPAR transiently expressed in HEK-293 cells. Arrow shows PL-PPAR construct;

FIG. 13 shows cellular spreads with PL-PPAR protein predominantly localized to the nucleus in the presence of CTZ. 13A. NIH3T3 cells; and 13B. ECV304 cells FIG. 14 shows activation of cloned M1 receptors leading to IkB-PL degradation in CHO-K1 cells upon stimulation with carbachol.

FIG. 15 shows activation of cloned melanocortin 4 (MC4) receptors leading to IkB-PL degradation in CHO-K1 cells.

FIG. 16 shows activation of the chemokine receptor CCR3 leading to IkB-PL degradation in CHO-K1 cells by eotaxin.

FIG. 17 shows EGFR activation as a measure of cell viability in HeLa cells.

FIG. 18 shows activation of the EGF receptor by EGF leading to IkB-PL degradation in HeLa cells.

DETAILED DESCRIPTION OF THE INVENTION

Figure 7:
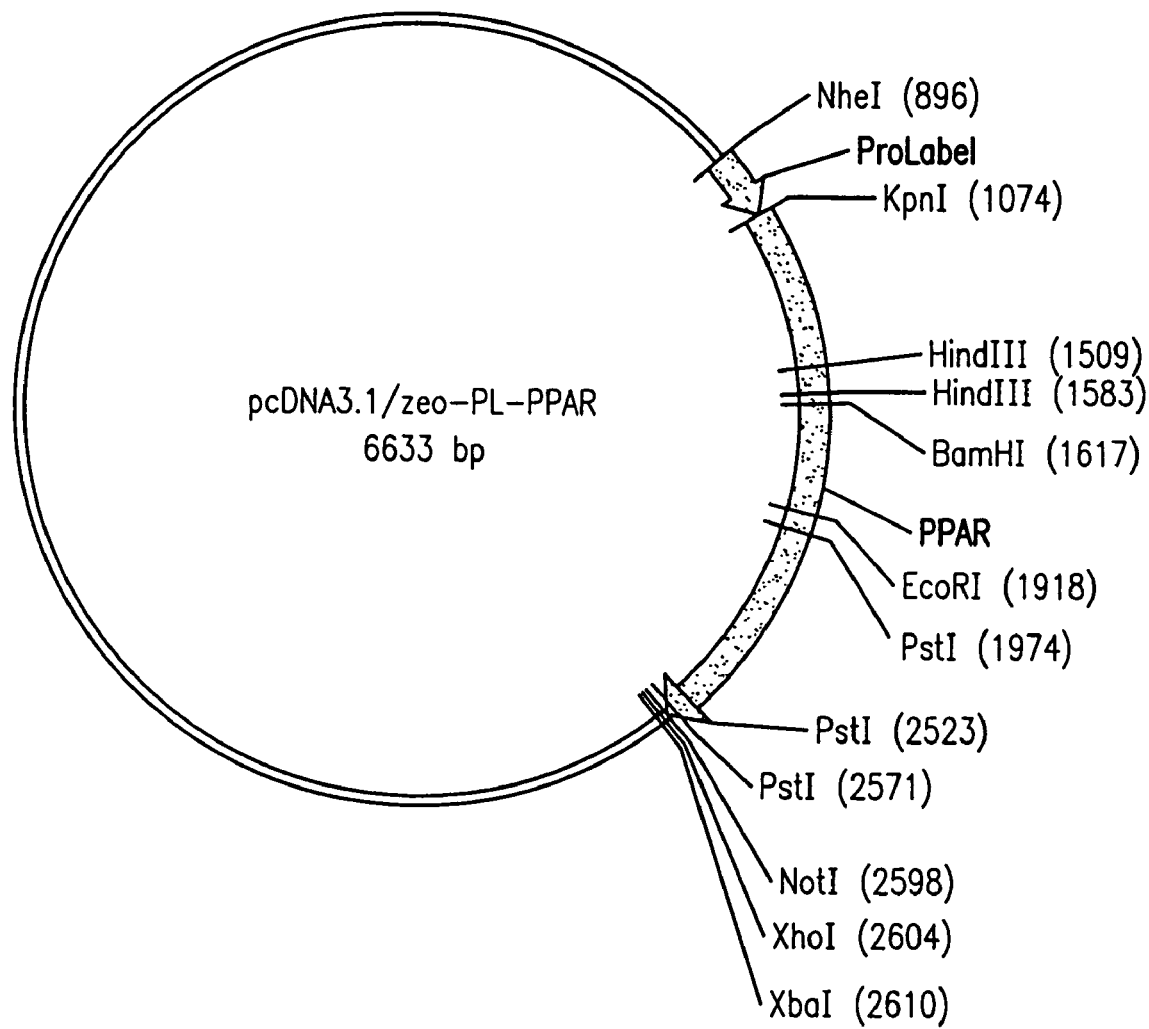
FIG. 7 is a map of the pcDNA3.1-PL-PPAR DNA construct.

Methods and compositions, as well as systems employing such methods and compositions, are provided for determining a cellular event, such as the status of a protein(s) of interest. The method permits the determination of the status of a fusion protein as the surrogate of the cellular event, as reflected by equating the fusion protein with the protein of interest associated with the cellular event. The method relies upon the use of an enzyme small fragment, referred to as the enzyme donor (ED) or as Prolabel (PL), as part of a fusion protein and a larger enzyme fragment, referred to as the enzyme acceptor (EA), where the complexing of the ED (or PL) and the EA provide for an active enzyme in the absence of other entities holding the fragments in juxtaposition. The enzyme activity in the sample acts as a surrogate for the cellular event in the cell as reflected by the activity of the ED (or PL) in complexing with the EA and forming an active enzyme. Events that result in (1) the expression of the fusion protein or (2) modify the fusion protein with a change in activity of the ED (or PL) in complexing or when complexed with the EA, can be measured as an indication of changes in the cell. The small enzyme fragment is referred to as ED or PL throughout this application.

The enzymes and their fragments are required to have a number of characteristics. The fragments should be substantially inactive, in that there should be little, if any, background with only one fragment present in the presence of substrate. Secondly, the fragments have sufficient affinity for each other, that in the absence of other binding, e.g. by entities fused to the fragments, the fragments will combine to provide an active enzyme. Various enzymes are known that fulfill these criteria and additional enzymes may be developed in accordance with known technologies. Enzymes that fit these criteria include β-galactosidase (See, U.S. Pat. No. 4,708,929), ribonuclease A (See, U.S. Pat. No. 4,378,428), where the smaller fragment may come from the amino or carboxy terminus or enzymes that have small peptide cofactors, such as adenovirus proteases (See, U.S. Pat. No. 5,935,840). To identify other enzymes that can serve in place of the above enzymes, enzyme genes may be cleaved asymmetrically to define a small and large fragment and expressed in the same and different cells. In the presence of the substrate, the cells producing both fragments would catalyze the reaction of the substrate, while there should be little, if any turnover, with the individual fragments. Alternatively, one may express the fragments individually and if there is no reaction, combine the mixtures to see whether an enzyme-catalyzed reaction occurs. Enzymes of interest are those that are below about 300 kDa, generally below about 150 kDa, where the small fragment will be under about 125 amino acids, generally under about 100 amino acids and preferably under about 75 amino acids. Depending on the enzyme the ED (or PL) may be as small as 10 amino acids, usually being at least about 25, more usually at least about 35 amino acids. With this criterion in mind, the fragments that are screened can be selected to provide the appropriately sized small fragment.

Each of the enzymes will have an appropriate substrate. β-galactosidase uses effectively fluorescers having phenolic groups that are etherified with a β-galactosyl group; Ribonuclease A employs fluorescer modified nucleotides, exemplified by 5'-O-acetyl 2'-O-(tetrahydropyran-2-yl)uridine 3'-(4-methylumbelliferon-7-yl) ammonium phosphate; adenovirus proteinase employs oligopeptides such as -(L, I, M)-X-G-G/X- (SEQ ID NO:7) or -(L, I, M)-X-G-X/G- (SEQ ID NO:8), where the vertical line denotes the position of cleavage; the P3 (X) position appears to be unimportant for cleavage (Anderson, C. W., *Virology*, 177;259 (1990); Webster, et al., *J. Gen. Virol.*, 70;3225 (1989)) and the peptide substrate can be designed to provide a detectable signal, e.g. using fluorescence resonance energy transfer, by having a fluorescer and a quencher on opposite sides of the cleavage site.

Since β-galactosidase is paradigmatic of the peptides used in the subject invention, demonstrating the criteria for having two peptides that when combined complex non-covalently to form an active enzyme, this enzyme will be frequently referred to hereafter as illustrative of the class, except for those situations where the different enzymes must be considered independently.

The method comprises after performing whatever changes, if any, in environment are to be evaluated, providing together the fusion protein with an enzyme acceptor in the presence of a detectable substrate, where the enzyme activity is measured. The amount of enzyme product produced is related to the activity of the ED in binding to the EA. The enzyme activity will be influenced by degradation of the fusion protein, binding of the fusion protein to a compound complexing with the protein of interest, modification of the fusion protein, transport of the fusion protein, and the like. One can also measure the rate of expression, transcription and translation, resulting from a promoter, by having a protease stable fusion protein and the expression level of a protein, as a result of the rate of formation and degradation of the fusion protein.

The systems and its subcomponents are provided for cellular monitoring, normally intracellular monitoring, of cellular activities, such as expression, degradation, translocation and complexing with other cellular components. Toward this end, components are provided that allow for the introduction of genetic constructs into host mammalian cells comprising an expression construct with a transcriptional regulatory region functional in mammalian cells and, under the transcriptional regulation of the regulatory region and a sequence encoding an inactive ED fragment capable of independent complexation with an EA fragment of the enzyme to form an active enzyme. Included with the construct is the EA fragment as a protein, an expression construct, or the expression construct in a cell, particularly integrated into the genome of the cell. Therefore, the two parts necessary for a functional enzyme are provided, with the second fragment either directly as the active protein or indirectly by expression in a cell. Also included in the system is an enzyme substrate that upon enzymatic catalyzed reaction, e.g. hydrolysis, releases a detectable product. Cells are also included in which the transcription construct(s) are functional and produce the fusion protein.

The β-galactosidase enzymes and its fragments (See, U.S. Pat. No. 4,708,929) are required to have a number of characteristics. The fragments are substantially inactive individually, in that there is little, if any, background with only one fragment present in the presence of substrate. Secondly, the fragments have sufficient affinity for each other, that in the absence of other binding, e.g. by entities fused to the fragments, the fragments will combine to provide an active enzyme. The small fragment ("ED" or "PL") will not interfere with the biological activity of the gene to which it is fused, the resulting fusion protein folding properly and retaining active sites of activity, including enzyme activity, binding activity to other proteins, translocation capability, etc. ED will usually be at least about 37, usually at least about 40 amino acids, and usually not more than about 110, more usually not more than about 90.

The substrates may provide for a fluorescent product, chemiluminescent product, electrochemical detectable product, etc. β-galactosidase uses, effectively as substrates, fluorescers having phenolic groups that are etherified with a β-galactosyl group. Colorimetric and fluorometric substrates that produce precipitatable products can also be used to image translocation.

The host cells comprising the fusion construct find many uses. The fusion protein may be used to determine the stability of the protein expressed by the gene fused to the ED (or PL) sequence in the host cell, the degree to which the protein is complexed in the host cell, the translocation of the fusion protein to a particular compartment of the host cell, the response of the fusion protein to changes in the nature of the cell and/or the environment of the cell. In effect, the fusion protein serves as a surrogate for the natural protein. In some instances, the host cell may not express the protein, where one is interested in the effect the protein may have on one or more pathways in the host. By knowing the amount of the fusion protein present in the host cell, one can determine the response of the fusion protein to the host cell and its environment and by extrapolation the natural protein. Because one can measure the amount of the fusion protein as a surrogate for the natural protein, one can determine the effect of drugs or other changes in the host cell environment on the protein. In this way, one can screen drugs for their effect on the protein, on pathways that affect the protein, how the drugs affect the proteins' interaction with other proteins, and the like. In addition, one can determine the effect of differentiation, neoplasia, hyperplasia, physical changes in environment, etc. on the status of the protein of interest.

The system can be initially used to determine whether the gene to be inserted results in a fusion protein that is biologically active to serve as a surrogate for the natural protein. The activity of the fusion protein may be determined by using host cells in which the expression of the natural protein does not occur, such as cells in which both copies of the natural protein have been knocked-out, where antisense RNA is added to the host cell that inhibits the natural protein but not the fusion protein, e.g. as to the non-coded 3'-region or includes the 5'-methionine codon, inhibits a transcription factor necessary for the natural protein, where the fusion protein has a different transcriptional regulatory region, if an enzyme, is shown to bind to its natural substrate and catalyze its reaction at a rate reasonably commensurate with the natural enzyme or, if not an enzyme, binds with an appropriate affinity to the proteins the natural protein binds to, etc.

The user of the system introduces the gene of interest into the genetic construct provided in the system. By having a multiple cloning site, the gene is manipulated so as to be inserted into the multiple cloning site in the correct orientation and in reading frame with the ED (or PL) sequence. Usually, there will be a linker of not more than 3 codons, preferably not more than about 2 codons, as a result of the nucleotides present in the multiple cloning site remaining between the ED sequence and the gene of interest. As indicated, the vector that is provided may include the transcriptional and/or translational termination sequences, a polyadenylation sequence, or other sequence that encodes a function, e.g. chelating, transamination, prenylation, farnesylation, geranylation, etc. Once the fusion protein construct has been completed, the construct may then be introduced into the host cell. The host cell may have a construct expressing the EA or, if not, such a construct may be added for transient expression or for integration into the genome and stable expression. Alternatively, a lysate may be prepared and, as appropriate, the EA added. The substrate that is chosen may be able to permeate the cell membrane, so that the substrate will be present in the cell in a non-rate-limiting amount. Alternatively, as indicated above, a lysate may be prepared and the substrate added to the lysate.

The host cell may naturally have the protein of interest or the protein of interest may be provided using an expression construct and adding the expression construct to the host cell. Rather than the protein of interest, a different protein may be provided using an expression construct, where the different protein is involved with a pathway with which the protein of interest is associated. In some instances, the expression construct may serve to augment the amount of a particular protein.

After the necessary modifications of the host cells have been accomplished, one may then proceed with the use of the host cells. For example, after performing whatever changes, if any, in environment of the host cells are to be evaluated, one would contact the fusion protein with an EA in the presence of a detectable substrate, where the enzyme activity is measured. The amount of enzyme product produced is related to the activity of the ED in binding to the EA. The enzyme activity will be influenced by degradation of the fusion protein, binding of the fusion protein to a compound complexing with the protein of interest, modification of the fusion protein, transport of the fusion protein, and the like. One can also measure the rate of expression, transcription and translation, resulting from a promoter, by having a protease stable fusion protein and measuring the expression level of the fusion protein, as a result of the rate of formation and degradation of the fusion protein.

The changes in the activity of the ED can be a result of the degradation of the fusion protein, by ubiquitination followed by degradation, protease degradation, denaturation, or other process. Alternatively, activity can be modified as a result of complex formation between the protein of interest and another protein. Activity can also be modified due to modification of the fusion protein, where the modification may result in complexing with another protein, change in the fusion protein conformation, presence of a substituent that changes the activity of the ED, or the like. Also, transport of the fusion protein to a compartment in the cell can result in a change in the measurable activity of the ED in the cell or in the compartment. In addition, where the modification affecting the ED activity is part of a pathway, the change in ED activity can be related to the events in the pathway. The fusion protein may comprise a protein of interest, a fragment of the protein of interest, a different polypeptide to represent the protein of interest or may be an intermediate for measuring some other protein or other activity, where when other than the natural protein is used, the fragment or alternative protein acts as a surrogate or mimetic.

Protein transport or translocation in the cell from the ribosome in the cytoplasm to another compartment, organelle or site, e.g. nucleus, cell membrane, proteasome, mitochondria, lysosome, Golgi, etc., can be of great importance to the biological properties of the protein and the cellular pathways of the cell. For protein transport, one can use leader sequences at the N terminus of the fusion protein from proteins that are known to be translocated to particular sites. One may also use coding sequences that result in modification of the fusion protein for binding the fusion protein to the cell membrane, such as sequences resulting in prenylation, myristoylation, farnesylation, etc. By providing for EA and substrate in the cell, depending upon the site of the fusion protein, one may be able to detect the presence of the fusion protein at the particular site.

The steps employed by the subject invention comprise: (1) preparing the fusion protein gene and expression construct by insertion of the gene of interest into the multiple cloning site of the genetic construct provided as part of the system; (2) introducing the expression construct comprising the fusion protein into a selected cell host, provided by the system or selected by the user; (3) optionally, also introducing an expression construct encoding EA, if not previously present as part of the host cells provided with the system; (4) incubating the transformed cell host under conditions that permit expression and cell viability; (5) (i) adding an intracellular substrate or (ii) lysing the cell host and adding EA and a substrate; and (6) measuring the turnover rate of production of product as a measure of a cellular event, usually as an indication of the status of the protein of interest. When intact cells are used, the detectable product may be detected as to a compartment, using cameras, microscopes or other device for visual detection. When providing for expression of EA, one will generally use a highly active promoter to ensure that there is a sufficient amount of the EA present in the cell to complex substantially all of the ED present, thus the EA promoter should be at least about twice as active as the ED promoter. When adding EA to the lysate, the same consideration is present, so that usually a large excess of EA to ED will be added, usually at least about two-fold excess, frequently at least about five-fold excess, and the excess may be 20-fold or greater.

For expression constructs and descriptions of other conventional manipulative processes, See, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The first component of the subject invention is the fusion protein and its expression construct. The ED may be at the C-terminus, the N-terminus or in between the termini. Therefore, there may be one or more ED sequences in the fusion protein to enhance the number of ED units present per fusion protein to increase the observed signal with the fusion protein molecules present. The ED may come from the N-terminus or C-terminus of the β-galactosidase enzyme.

The particular site of the ED in the fusion protein will depend upon the ability to include the ED in the coding sequence without significant reduction in the natural activity of the protein of interest. Thus, depending upon how much is known about the protein of interest, its structure, site(s) of binding to other entities, the folding pattern, as to loops, β-sheets and β-helices, the manner in which the ED activity will be modulated, e.g. degradation, steric interference of binding with EA by another entity, modification resulting in changes in conformation or charge, etc., the ED will be situated to provide the optimized response. For degradation, it will frequently not matter at what site the ED is situated, this is also likely to be true in many cases for steric interference, so long as the protein of interest retains its natural conformation and susceptibility to degradation and the ED retains its ability to activate the EA.

For translocation from the ribosome in the cytosol, depending on the nature of the protein of interest, it will be desirable to have a leader sequence that is recognized for such translocation. One may provide for the leader sequence at the 5' terminus of the ED sequence in the direction of transcription, so as to be in reading frame with the ED sequence. For proteins of interest comprising a leader sequence, one can provide for a multiple cloning site 5' of the ED sequence for insertion of the native leader sequence in reading frame with the ED sequence. Alternatively, one may provide for a leader sequence associated with the desired translocation in a genetic construct, where the leader sequence may not be the natural sequence, but will fulfill the same function as the leader sequence, e.g. translocation to a membrane, nucleus, lysosome, mitochondria, etc.

The gene encoding the fusion protein will be part of an expression construct. The gene is positioned to be under transcriptional and translational regulatory regions functional in the cellular host. In a few instances, the regulatory regions may be the native regulatory regions of the gene encoding the protein of interest, where the fusion protein will be on an extrachromosomal or episomal element or randomly integrated into the genome of the host cell. In those cells in which the native protein is present and expressed, the fusion protein will be competing with the native protein for transcription factors for expression. The site of the gene in an extrachromosomal element or in the chromosome may vary as to transcription level. Therefore, in most instances, the transcriptional initiation region will be selected to be operative in the cellular host, but may be from a virus or other source that will not significantly compete with the native transcriptional regulatory regions or may be associated with a different gene from the gene for the protein of interest, which gene will not interfere significantly with the transcription of the fusion protein.

It should be understood that the site of integration of the expression construct, if integrated into a host chromosome, would affect the efficiency of transcription and, therefore, expression of the fusion protein. One may optimize the efficiency of expression by selecting for cells having a high rate of transcription or one can modify the expression construct by having the expression construct joined to a gene that can be amplified and coamplifies the expression construct, e.g. DHFR in the presence of methotrexate.

There are a large number of commercially available transcriptional regulatory regions that may be used and the particular selection will be selected in accordance with the function of the vector and the genes of interest for which the vector is designed. Also, the manner in which the fusion gene construct is introduced into the host cell will vary with the purpose for which the fusion gene is being used. The introduction of the construct may be performed in vitro or in vivo and will include situations where cells transformed in culture are then introduced into the mammalian host or a virus carrying the construct may be introduced into a mammalian host, particularly where the virus is tropic for a particular type of cell. The transcriptional regulatory region may be constitutive or inducible. In the former case, one can have a steady state concentration of the fusion protein in the host cell, while in the latter case one can provide going from the substantially total absence (there is the possibility of leakage) to an increasing amount of the fusion protein until a steady state is reached. With inducible transcription, one can cycle the cell from a state where the fusion protein is absent to a state where the steady state concentration of the fusion protein is present.

Vectors for introduction of the construct include an attenuated or defective DNA virus, such as but not limited to, herpes simplex virus (HSV), papillomavirus, Epstein Barr virus (EBV), adenovirus, adeno-associated virus (AAV), and the like. Defective viruses, appropriately packaged, which entirely or almost entirely lack viral genes, are preferred. Defective virus is not infective after introduction into a cell. Use of defective viral vectors, particularly tropic for particular cell types, allows for administration to cells in a specific, localized area of the host, without concern that the vector can infect other cells. Thus, a particular locus can be specifically targeted with the vector. Specific viral vectors include: a defective herpes virus 1 (HSV1) vector (Kaplitt et al., 1991, *Molec. Cell. Neurosci.* 2:320-330); an attenuated adenovirus vector, such as the vector described by Stratford-Perricaudet et al. (1992, *J. Clin. Invest.* 90:626-630 a defective adeno-associated virus vector (Samulski et al., 1987, *J. Virol.* 61:3096-3101; Samulski et al., 1989, *J. Virol.* 63:3822-3828). Alternatively, the virus may include a promoter for expression of a gene that is necessary for replication of the virus that is limited to particular types of cells comprising the transcription factors essential for expression. This construct would be for monitoring cells that have such transcription factors.

The vector may be introduced in vitro and in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection. (Felgner, et. al., 1987, *Proc. Natl. Acad. Sci.* (*U.S.A.*), 84:7413-7417; see Mackey, et al., 1988, *Proc. Natl. Acad. Sci.* U.S.A., 85:8027-8031)). The use of cationic lipids may promote encapsulation of negatively charged nucleic acids, and also promote fusion with negatively charged cell membranes (Felgner and Ringold, 1989, *Science*, 337:387-388). Lipofection into the nervous system in vivo has recently been achieved (Holt, et. al., 1990, *Neuron*, 4:203-214). The use of lipofection to introduce exogenous genes into the nervous system in vivo has certain practical advantages. Lipids may be chemically coupled to other molecules for the purpose of targeting (see Mackey, et. al., 1988, supra). Targeted peptides or non-peptide molecules can be coupled to liposomes chemically.

It is also possible to introduce the vector in vitro and in vivo as a naked DNA plasmid, using calcium phosphate precipitation, electoporation or other known agent. Alternatively, the vector containing the gene encoding the fusion protein can be introduced via a DNA vector transporter (see, e.g., Wu et al., 1992, *J. Biol. Chem.*, 267:963-967; Wu and Wu, 1988, J. Biol. Chem. 263:14621-14624; Hartmut et al., Canadian Patent Application No. 2,012,311, filed Mar. 15, 1990).

Vectors are introduced into the desired host cells in vitro by methods known in the art, e.g., transfection, electroporation, microinjection, transduction, cell fusion, DEAE dextran, calcium phosphate precipitation, lipofection (lysosome fusion), use of a gene gun, using a viral vector, with a DNA vector transporter, and the like.

Advantages associated with in vivo introduction of the fusion protein expression construct are that one has the expression of the fusion protein in a natural setting where the factors normally associated with the status of the cell are present. For example, if one were interested in knowing how a drug acted on a cell type in relation to the protein of interest, by testing the drug in vivo, one is able to determine the response of the protein of interest under natural conditions. A disadvantage is that one will usually be unable to control the level of expression and will be looking at the average level over a number of cells that differ as to the efficiency of expression and potentially the response to the environment.

Expression vectors containing the fusion protein gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of the fusion protein gene inserted in an expression vector can be detected by nucleic acid hybridization using probes comprising sequences that are homologous to the fusion protein gene. In the third approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. In the fourth approach, recombinant expression vectors can be identified by assaying for the activity of the fusion protein gene product expressed by the recombinant expression vector.

One may use promoters that are active for a short time, such as viral promoters for early genes, for example, the human cytomegalovirus (hCMV) immediate early promoter. Other viral promoters include but are not limited to strong promoters, such as cytomegaloviral promoters (CMV), SR.alpha. (Takebe et al., Mole. Cell. Biol. 8:466 (1988)), SV40 promoters, respiratory syncytial viral promoters (RSV), thymidine kinase (TK), beta-globin, etc. Alternatively, an inducible promoter can be used.

A large number of promoters have found use in various situations, for various purposes and for various hosts. Many promoters are commercially available today. Expression of the fusion protein may be controlled by any promoter/enhancer element known in the art, but these regulatory elements must be functional in the host or host cell selected for expression. Promoters which may be used to control fusion gene expression include, but are not limited to, the SV40 early promoter region (Benoist and Chambon, 1981, *Nature,* 290: 304-310), the promoter contained in the 3' long terminal repeat of Rous sarcoma virus (Yamamoto, et al., 1980, *Cell,* 22:787-797), the herpes thymidine kinase promoter (Wagner et al., 1981, *Proc. Natl. Acad. Sci. U.S.A.,* 78:1441-1445), the regulatory sequences of the metallothionein gene (Brinster et al., 1982, *Nature,* 296:39-42); and the following animal transcriptional control regions, which exhibit tissue specificity and have been utilized in transgenic animals: elastase I gene control region which is active in pancreatic acinar cells (Swift et al., 1984, *Cell,* 38:639-646; Ornitz et al., 1986, Cold Spring Harbor *Symp. Quant. Biol.,* 50:399-409; MacDonald, 1987, Hepatology, 7:425-515); insulin gene control region which is active in pancreatic beta cells (Hanahan, 1985, *Nature,* 315: 115-122), immunoglobulin gene control region which is active in lymphoid cells (Grosschedl et al., 1984, Cell 38:647-658; Adames et al., 1985, *Nature,* 318:533-538; Alexander et al., 1987, *Mol. Cell. Biol.,* 7:1436-1444), mouse mammary tumor virus control region which is active in testicular, breast, lymphoid and mast cells (Leder et al., 1986, *Cell,* 45:485-495), albumin gene control region which is active in liver (Pinkert et al., 1987, *Genes and Devel.,* 1:268-276), alpha-fetoprotein gene control region which is active in liver (Krumlauf et al., 1985, *Mol. Cell. Biol.,* 5:1639-1648; Hammer et al., 1987, *Science,* 235:53-58), α1-antitrypsin gene control region which is active in the liver (Kelsey et al., 1987, *Genes and Devel.* 1:161-171), β-globin gene control region which is active in myeloid cells (Mogram et al., 1985, *Nature,* 315:338-340; Kollias et al., 1986, *Cell,* 46:89-94), myelin basic protein gene control region which is active in oligodendrocyte cells in the brain (Readhead et al., 1987; *Cell,* 48:703-712), myosin light chain-2 gene control region which is active in skeletal muscle (Sani, 1985, *Nature* 314:283-286), prostate specific antigen control region, which is active in prostate cells (U.S. Pat. Nos. 6,197,293 and 6,136,792), and gonadotropic releasing hormone gene control region which is active in the hypothalamus (Mason et al., 1986, *Science,* 234:1372-1378). Alternatively, expression of the fusion protein gene can be under control of an inducible promoter, such as metallothionein promoter, which is induced by exposure to heavy metals. For control of the gene transfected into certain brain cells, a glucocorticoid inducible promoter can be used, since glucocorticoids can cross the blood-brain barrier. Alternatively, an estrogen inducible promoter, which would be active in the hypothalamus and other areas responsive to estrogen, can be used. In addition, tet inducible promoters may be employed. Other promoters are available where the transcription may be terminated by means of an exogenous agent. The present invention contemplates the use of any promoter inducible or terminable by a pharmacologic agent that can cross the membrane and for neuronal cells in vivo, the blood-brain barrier and influence transcription.

Vectors containing DNA encoding the following proteins, for example, have been deposited with the American Type Culture Collection (ATCC) of Rockville, Md.: Factor VIII (pSP64-VIII, ATCC No. 39812); a Factor VIII analog, "LA", lacking 581 amino acids (pDGR-2, ATCC No. 53100); t-PA and analogs thereof (see co-pending U.S. application Ser. No. 882,051); VWF (pMT2-VWF, ATCC No. 67122); EPO (pRK1-4, ATCC No. 39940; pdBPVMMTneo 342-12 (BPV-type vector) ATCC No. 37224); and GM-CSF (pCSF-1, ATCC No. 39754).

A number of commercial mammalian vectors are available with different capabilities, different promoters, msc's, and selection genes. pYACneo (Replicon), pAdvantage, pSI (SV40p), pTarget, pGIneo (Promega), Vitality hrGFP (Stratagene), pCMS-EGFP-1, pEGFP-NI (BD Biosciences), pVIT-ROms (Invivogen), pRK-5 GFP (Fujisawa) and pCruz 22 (Santa Cruz) (supplier).

The vector will include the fusion gene under the transcriptional and translational control of a promoter, usually a promoter/enhancer region, optionally a replication initiation region to be replication competent, a marker for selection, as described above such as antibiotic resistance, and may include additional features, such as PCR initiation sites, an expression construct providing constitutive or inducible expression of EA, or the like. As described above, there are numerous vectors available providing for numerous different approaches for the expression of the fusion protein in a host.

The host cells will be selected to provide the necessary transcription factors for expression of the fusion protein and the other components for the purposes of the determination. The host cells will also be selected toward providing an environment resembling the environment being simulated. In some cases primary cells may be employed, both those maintained in culture and obtained directly from a patient, but usually one will use cell lines, whether oncogenic or non-oncogenic. Established cell lines are useful, since the cell lines can provide the desired environment and allow for direct comparisons between studies, which comparisons may not be available where using primary cells from patients. As indicated previously, the host cells may be modified to express a protein that influences the protein of interest, for example, by being associated with a pathway with which the protein of interest is associated. In some instances a host cell will be selected that lacks a particular protein, such as a receptor, so that by introducing an expression construct for the receptor, one can control the expression of the particular protein. These genetic modifications may be carried out prior to, concomitantly with or subsequent to the introduction of the construct expressing the fusion protein. The genetic modifications may be transient or substantially permanent, with cells being selected that provide the desired level of expression and control of expression.

The subject system employs mammalian cells, including domestic animal cells, e.g. murine, bovine, canine, feline, porcine, lagomorpha, etc., more particularly, primates, e.g. monkeys, apes, humans, etc. Established cell lines, including transformed cell lines, are suitable as hosts. Normal diploid cells, cell strains derived from in vitro culture of primary tissue, as well as primary explants (including relatively undifferentiated cells such as hematopoietic stem cells) are also suitable. Embryonic cells may find use, as well as stem cells, e.g. hematopoietic stem cells, neuronal stem cells, muscle stem cells, etc. Candidate cells need not be genotypically deficient in a selection gene so long as the selection gene is dominantly acting. The host cells preferably will be established mammalian cell lines. For stable integration of vector DNA into chromosomal DNA, and for subsequent amplification of the integrated vector DNA, both by conventional methods, CHO (Chinese Hamster Ovary) cells are convenient. Alternatively, vector DNA may include all or part of the bovine papilloma virus genome (Lusky et al., 1984, Cell 36:391-401) and be carried in cell lines such as C127 mouse cells as a stable episomal element. Other usable mammalian cell lines include HeLa, COS-1 monkey cells, melanoma cell lines such as Bowes cells, mouse L-929 cells, mouse mammary tumor cells, 3T3 lines derived from Swiss, Balb-c or NIH mice, BHK or HAK hamster cell lines and the like.

Cell lines may be modified by knocking out specific genes, introducing specific genes, e.g. the EA coding gene, enhancing or diminishing the expression of a protein or the like. The modification may be transient, as in the case of introduction of antisense DNA or RNAi or may be permanent, by deleting a gene, introducing a gene encoding the antisense mRNA of the target protein, adding a dominant recessive gene, or the like. Research animals may be employed of various strains, where the strains are a result of naturally occurring mutations and breeding or using genetic modifications of embryonic or other cells with a resulting genetically modified host. Knockout mice are extensively described in the literature. One may use the intact host, tissue from the intact host or cells from the intact host for the purposes of this invention. Illustrative of the development of knockout and knockin mice are Nozawa, et al., *Transplantation*, 2001, 72:147-55; Ferreira, et al., *Blood*, 2001 98:525-32; Kotani, et al., *Biochem. J.*, 2001, 357:827-34; Zhou, et al., *Int. J. Radiat. Biol.*, 2001, 77:763-72; and Chang, et al., *Mol. Cell. Endocrinol.*, 2001, 180:39-46, and references cited therein, to provide only a few of the large number of publications concerning genetically modified mice. In addition one may use hybridomas, where a first cell having the desired gene(s) is fused with an immortalized cell under conditions where the chromosomes from the first cell are stably maintained. The gene(s) could be transcription factors, proteins of interest, e.g. human proteins in a non-human host cell, or provide for enhanced expression of a protein.

The status of all cellular proteins, particularly intracellular proteins, can be determined in accordance with this invention to the extent that the fusion protein can serve as a surrogate for a protein of interest, since all proteins will be subject to some modification, e.g. degradation. By status is intended a property of the protein, such as location, amount, complexation with other proteins, modification, e.g. phosphorylation or dephosphorylation, etc. Any modification that changes the ED activity of a biologically active fusion protein under the conditions of the assay will be subject to detection. These modifications include complex formation with one or more proteins, chemical modification, such as the removal or addition of groups, such as acetyl, phosphate, methyl, sulfate, fatty acid esters, alkoxylation, etc., translocation, where one can detect the difference in activity in a compartment, and the like. For the most part, the proteins of interest will be associated with a health function, such as the effect of an infectious disease, genetic defect, mutation, response to a drug, neoplasia, inflammatory response, etc. Thus, the change in the activity of the ED of the fusion protein will be relevant to a physiological function in the diagnosis and treatment of mammalian hosts and to that extent can indicate the status of the cell, such as neoplastic, differentiation, stress, etc.

Degradation can be readily distinguished from other modifications by using additional assays. Knowing the activity of the fusion protein with the EA, one can isolate the fusion protein using antibodies or other binding compounds for sequestering the fusion protein and determining the number of fusion proteins. The difference between the activity from the total fusion protein present in the lysate and the observed activity will be an indication of interactions other than degradation of the fusion protein. Intracellularly, one would have to know the amount of the fusion protein during the cellular cycle, so that the signal that is observed can be related to events other than degradation. The total intracellular amount can be determined using a lysate as described above and the signal observed with different amounts of the fusion protein in the absence or presence of modifications graphed to be used for comparison of results with assays.

The presence of the construct in the cell or a compartment of the cell can be determined using visual analyses on the intact cells, employing cameras, e.g. CCD cameras, microscopes or other devices that allow for integration over the entire cell of the detectable signal or only as to one compartment. For example, one can readily detect the concentration of the detectable signal in the nucleus as compared to the cytosol and vice versa. FACS machines may be used to integrate the signal from intact cells, where the enzyme reaction is allowed to proceed for a predetermined amount of time, quenched and the cells analyzed.

Also secreted proteins can be determined while they are intracellular. Prior to being transported from the Golgi to the surface membrane, a number of steps must occur and one can determine the number of such molecules in the cell and whether they are complexed with other proteins, e.g. docking protein.

The efficiency of transcription can also be determined by using a fusion protein that is stable, that is, is not subject to significant modification during the period of the assay. By using a stable protein, such as a prion, â-amyloid, synthetic polypeptides, such as collagen, keratin or elastin motifs, or providing for secretion into a non-proteolytic environment, one can determine the rate of expression from a regulatory region of interest. One may introduce a construct with the appropriate regulatory region, where the native and constructed expression systems would both be active, while the fusion protein would indicate the effectiveness of the expression system. In this instance, one would usually be interested in the effect of a change, e.g. environment, genome, etc., on the transcriptional activity of the regulatory region. One could then evaluate the effect of an agent on the transduction of a signal as a result of a binding event at the cell surface, the effect of an intracellular inhibitor, or the effect of a second pathway that involves a first pathway.

Of the protein categories of interest, transcription factors, inhibitors, regulatory factors, enzymes, membrane proteins, structural proteins, and proteins complexing with any of these proteins, are of interest. Specific proteins include enzymes, such as the hydrolases exemplified by amide cleaving peptidases, such as caspases, thrombin, plasminogen, tissue plasminogen activator, cathepsins, dipeptidyl peptidases, prostate specific antigen, elastase, collagenase, exopeptidases, endopeptidases, aminopeptidase, metalloproteinases, including both the serine/threonine proteases and the tyrosine proteases,; hydrolases such as acetylcholinesterase, saccharidases, lipases, acylases, ATP cyclohydrolase, cerebrosidases, ATPase, sphingomyelinases, phosphatases, phosphodiesterases, nucleases, both endo- and exonucleases,; oxidoreductases, such as the cytochrome proteins, the dehydrogenases, such as NAD dependent dehydrogenases, xanthine dehydrogenase, dihydroorotate dehydrogenase, aldehyde and alcohol dehydrogenase, aromatase,; the reductases, such as aldose reductase, HMG-CoA reductase, trypanothione reductase, etc., and other oxidoreductases, such as peroxidases, such as myeloperoxidase, glutathione peroxidase, etc., oxidases, such as monoamine oxidase, myeloperoxidases, and other enzymes within the class, such as NO synthase, thioredoxin reductase, dopamine β-hydroxylase, superoxide dismutase, nox-1 oxygenase, etc.; and other enzymes of other classes, such as the transaminase, GABA transaminase, the synthases, β-ketoacyl carrier protein synthase, thymidylate synthase, synthatases, such as the amino acid tRNA synthatase, transferases, such as enol-pyruvyl transferase, glycinamide ribonucleotide transformylase, COX-1 and -2, adenosine deaminase.

Kinases are of great significance, such as tyrosine kinases, the MAP kinases, the cyclin dependent kinases, GTP kinases, ser/thr kinases, Chk1 and 2, etc.

Also of interest are enzyme inhibitors, such as $\alpha_1$-antitrypsin, antithrombin, cyclophilin inhibitors, proteasome inhibitors, etc.

Other proteins of interest are the oncogenes, such as Src, Ras, Neu, Erb, Fos, Kit, Jun, Myc, Myb, Abl, Bcl, etc. Cytokines, such as the .interferons, $\alpha$-$\gamma$, interleukins, 1-19, and integrins, adhesins, TNF, receptors, hormones, colony stimulating factors, growth factors, such as epidermal growth factor, fibroblast growth factor, etc., bone morphogenetic proteins, developmental proteins, such as the Hox proteins, or other proteins binding to or regulating proteins binding to homeoboxes, e.g. the hedgehog proteins, basement membrane proteins, heat shock proteins, proteins containing Krupple and Kringle structures chaperonins, calcium associated proteins, e.g. calmodulin, calcineurin, etc., membrane channels, transporter proteins, etc.

Also of interest are the proteins associated with proliferation, such as the cyclins, cyclin dependent kinases, p53, RB, etc.

Neuronal proteins, such as $\beta$-amyloid, TNF, prion, APP, transporters, e.g. dopamine transporter, receptors, such as NMDA receptors, AMDA receptors, dopamine receptors, channels, etc.

Another class of proteins are the membrane receptors, particularly the cell membrane receptors, and the proteins associated with such receptors, such as G proteins, G protein complexed receptors, insulin receptor, growth factor receptors, EPO receptor, T cell receptor, immunoglobulins, CD4, CD8, etc. Other cytoplasmic membrane proteins of interest include major and minor histocompatibility complex proteins, adhesion proteins, channels, etc.

Another class of proteins is the transcription factors and their inhibitors or regulatory proteins, such as Adr Ace, Amt, AP, Atf, Att, Baf, Brn, Btf, C Ebp, C Jun, C Ets, CREB, CF, Chop, DP, E2F, Elk, Gata, Hnf, Iii A-H, Irf, NY Y, Otf, NFêB, NF-AT, Oct-1, Pea, Pit, PU, S, SP, Stat, Tef, TFIII, TFIIII, Ubf and Usf, while the inhibitors include Erk, IêB, LIF, Smad, RANTES, Tdg, etc., as well as other proteins associated with pathways that induce transcription factor synthesis, activation or inhibition.

Another class of proteins are the hormonal nuclear receptors, such as the PPAR proteins.

In some instances, housekeeping proteins will be of interest, such as the proteins involved in the tricarboxylic acid cycle, the Krebs cycle, glycogenesis, etc.

Various pathways will be of interest associated with the different proteins. Thus, pathways involving signal transduction as a result of ligand binding to a surface membrane protein receptor, vesicle formation and transport, multistage synthesis of cellular components, proteasomes, peroxisomes, spindle formation, tubulin assemblage, processing of ingested compounds, e.g. toxins, drugs, etc.

The cells comprising the subject constructs may be used to identify proteins associated with a pathway of interest, the effect of a change in environment, such as the presence of a drug or drug candidate, on the production of the protein of interest, changes in the regulation of expression, the effect of inhibiting expression of a protein, the regulation by a receptor of a cellular pathway and to that extent, compounds that affect the transduction of a signal by the receptor, the activation or deactivation of cellular pathways that affect the complex formation or degradation of the fusion protein, expression level of a protein, related to the rates of formation and degradation, etc. Where one is interested in a specific pathway for inducing transcription, the genetic construct will have the regulatory region of interest in association with the gene of interest.

Changes in environment include the presence of a chemical agent, e.g. drug, such as an antibiotic, enzyme inhibitor, receptor ligand, etc., change in the physical environment, such as temperature, atmosphere or pH, changes in the culture medium, such as addition or removal of nutrients, addition of non-aqueous solvents, etc.

For $\beta$-galactosidase, a number of substrates for $\beta$-galactosidase are known, where the product is fluorescent. The common substrates are $\beta$-D-galactopyranosyl phenols, such as fluorescein, mono- and di-substituted, o-nitrophenyl-$\beta$-D-galactoside, $\beta$-methylumbelliferyl-$\beta$-D-galactoside, X-gal, resorufin-$\beta$-D-galactoside, commercially available oxetanes, e.g. Galacto-Light Plus® kits (chemiluminescence) and chlorophenol red. The di-$\beta$-D-galactopyranosylfluorescein, and chlorophenol red- $\beta$-D-galactopyranoside may be used as intracellular markers.

The simplest procedure to describe is the use of cells in culture and analysis of the lysate. In this case, the cells are grown in culture. The fusion protein and other constructs, as appropriate, may be present in the cell integrated into the genome or may be added transiently by the various methods for introducing DNA into a cell for functional translation. The cells may be in culture or in vivo. These methods are amply exemplified in the literature, as previously described. By employing a marker with the fusion protein for selection of cells comprising the construct, such as antibiotic resistance, development of a detectable signal, etc., cells in culture comprising the fusion protein can be separated from cells in which the construct is absent. Once the fusion protein is being expressed, the environment of the cells may be modified, if desired. Candidate compounds may be added, ligand for receptors, surface membrane or nuclear, or the two of these may be added in combination, changes in the culture medium may be created, other cells may be added for secretion of factors or binding to the transformed cells, viruses may be added, or the like. Given sufficient time for the environment to take effect and/or taking aliquots of the culture at different time intervals, the cells may be lysed with a lysis cocktail comprising EA and enzyme substrate and the signal from the product read. One can then relate this result to the amount of fusion protein present, particularly by using standards where the lysate is spiked with different amounts of the fusion protein and the amount of active fusion protein determined. One would then have a graph relating signal to amount of active fusion protein in the lysate.

Where the cells are in a viable host, usually the cells or tissue from the host will be harvested and may be lysed, so that the methodology used for the culture will be the same. Selection of cells having the construct can be achieved by having an antibiotic resistance gene as part of the construct, so that cells can be selected using the antibiotic to avoid dilution of the sample by cells lacking the construct.

In cases of translocation or other event that allows for differential distribution of the ED, by providing the EA and substrate to the cell, one can microscopically determine the distribution of the ED. Where the translocation occurs from the cytosol to the nucleus, one can measure the signal from the nucleus and the cytosol independently, with one or both measurements providing the necessary information.

With cells having the EA and substrate present, one may determine the level of active ED present using a fluorescence activated cell sorter. By providing for a threshold level of signal, one can count the number of cells above that threshold and obtain a distribution pattern of the amount of ED in the cells. Other methods of measuring fluorescence as a bulk property or with individual cells are well known, such as confocal laser scanning cytometry.

For convenience, the systems are provided as kits that may include all or some of the major components of the assays. For example, a kit will include an expression construct as part of a vector, e.g. plasmid, virus, usually attenuated, where the expression construct may include a marker, a gene encoding a protein for integration, a replication initiation site, and the like. In addition to the expression construct, the kit will include EA or the equivalent, e.g. an expression construct for EA, substrate for β-galactosidase, and may in addition include one or more cell lines or primary cells, a graph of response in relation to the amount of ED present, buffer, etc. In some instances cells may be engineered to provide a desired environment, such as high levels of expression of a protein involved in a pathway of interest, such as surface membrane receptors, GPCRs, nuclear receptors, e.g. steroid receptors, transcription factors, etc. or may have been mutated, so as to have reduced levels of expression affecting the expression of the native protein of the fusion protein and one is interested in enhancing the level of expression.

As indicated, the subject method can be used in a variety of situations to great effect, since the ED is small enough to allow for functioning of the protein of interest as a fusion protein with ED, while allowing for ED to complex with EA to provide a functional enzyme.

The following examples are intended to illustrate but not limit the invention.

Experimental

Generation of IκB-ED Fusion Protein

The cDNAs encoding IκB and ED (FIG. 1) were amplified with Pfu DNA polymerase (Stratagene, CA). Both IκBα and IκB M were amplified using forward primer: 5'-CCGAAGCTTATGTTCCAGGCGGCCGAG-3' (SEQ ID NO: 1) and reverse primer: 5'-ATAGGATCCTAACGTCA-GACGCTGGCC-3' (SEQ ID NO: 2). These primers incorporated a Hind III at the 5' end and a Bam HI at the 3' end of the PCR products. Also, the stop codon of the IκB was removed in order to provide an open reading frame with ED. pCMV- IκB and pCMV- IκB M (CLONTECH, Calif.) used as PCR template. IκB M contains a serine to alanine mutation at amino acid residue 32 and 36. These two sites are critical to the phosphorylation of IκB, and the mutant results in the resistance of IκB to degradation (Brown, Gerstberger, Carlson, Franzoso, *Science*, 1995 Mar 10;267(5203):1485-8). ED, on the other hand was amplified using forward primer: 5'-ATAGGATCCATGAGCTCCAATTCACTGGCCG -3' (SEQ ID NO: 3) and reverse primer 5'-ATAAGAATGCGGC-CGCCTATTCGCCATTCAGGCTGCGC-3' (SEQ ID NO: 4). The forward primer incorporated a Bam HI site to the ED and the reverse primer incorporated a Not I site to the ED as well as a stop codon. The amplification was using the PCR program with denature DNA at 92° C. for 1 min, anneal at 52° C. for 1 min and then elongate at 72° C. for 2 min, followed by 29 cycles repeating in total. The amplified PCR products were ligated at the Bam HI site and the resulting fusion constructs were subcloned into a mammalian expression vector pCMV at the sites of Hind III and Not I resulting in the construct designated pCMV- IκB -ED. pCMV vector originated from pCMV-IκB α (CLONTECH, Calif.), where the IκB α was substituted by IκB -ED fusion construct. The pCMV-ED construct was obtained by inserting ED PCR product into the Bam HI site and Not I site following standard molecular biology procedure (Maniatis et al; supra).

Expression of ED Fusion Proteins in Cell Culture

HeLa cells were kept in culture in DMEM medium (GIBCO, Calif.) supplemented with 10% fetal bovine serum and 2 mM glutamine (GIBCO, Calif.). For transient transfection, cells were seeded into 6 well plate one day before experiment. For each well, 3 µl of Fugene 6 (Roche, Ind.) was diluted into 100_µl of serum free medium, and then 1_µg of plasmid DNA was added. The mixture was incubated at room temperature for 15 min before addition into wells dropwise. The plate was then incubated at 37° C. till the assay.

To detect ED activity, 24 hr after transfection, the culture medium was removed, and the cells lysed with 200 µl of cell lysis buffer (0.5% CHAPS, 10 mM potassium phosphate, 10 mM sodium chloride, pH 6.9). Then 30 µl of the cell lysate was transferred into 384-well plate, where 10 µl of EA reagent (0.18 mg/ml EA and 0.5% fetal bovine serum in EA core buffer (100 mM PIPES, 400 mM NaCl, 10 mM EGTA, 0.005% Tween, 150 mM NaOH, 10 mM Mg acetate, 14.6 mM NaN$_3$, pH 6.9)) was added. After 30 min incubation at room temperature, 15 µl of chemiluminescence substrate (4% of Galacton Star™ and 20% of Emerald II™ (Tropix) in EA core buffer) was added. The signal was read on Lumicount (Packard) or Fluoroskan (Labsystem) with integration time of 1 second per well.

In FIG. 2, three constructs were transfected into HeLa cells, they are pCMV-ED, pCMV- IκB -ED and pCMV- IκB M-ED, respectively. The non-transfected cells were also used as negative control. When ED was expressed as a fusion protein, the ED activity is readily detected, indicating that the fusion protein is relatively stable. However, when the ED is expressed alone, unfused, the ED activity dropped to the basal level, suggesting that the unfused ED is a very unstable peptide, and gets degraded quickly in cells.

TNFα-induced IκB-ED Degradation in HeLa Cells

HeLa cells were seeded into 24 well plate 24 hr before transfection. 0.25 µg DNA was transfected into each well using Fugene6 (Roche) following manufacture's protocol. 24 hr after transfection, cells were subjected to treatment of TNFα (Sigma) at various concentrations for 30 min. Then the culture medium was removed, and cells were lysed in 90 µl of cell lysis buffer. 30 µl of cell lysate was transferred into 384 well plate, where 10 µl EA reagent was added. Assay was performed in three replicates. The plate was incubated at room temperature for 30 min before addition of 15 µl chemiluminescence substrate. Plate was read 30 min after substrate addition. The untreated cells were normalized to 100% activity. As shown in FIG. 3, TNFα was able to decrease the ED activity in a dose dependent manner, which indicated the degradation of wild type IκB. Contrastingly, the mutant form did not show a dose dependent decrease of ED activity upon TNFα treatment, as expected. This result demonstrated that ED as a fusion tag did not change the IκB biological function, and was able to monitor IκB degradation in vivo. In addition, the IκB-ED degradation was specifically linked to the upstream component activation. Also confirmed was that the IκB-ED degradation was dependent on IκB phosporylation at 32 and 36 residues, the same way as un-tagged IκB.

IL-1-induced IκB-ED Degradation in HeLa Cells

It has been reported that IL-1 activation of cells results in NF-κB pathway activation through the induced degradation of IκB. To confirm that the ED labeled IκB in cells was able to monitor IL-1 pathway activation, HeLa cells was transiently transfected with pCMV- IκB -ED or pCMV- IκB M-ED the same way as described above in 24 well plates. Cells were then treated with IL-1 (Sigma) at various concentrations for 30 min then assayed for ED activity. As shown in FIG. 4, IκB -ED activity was decreased upon IL-1 treatment in a dose dependent manner, whereas the mutant form of IκB, IκB M-ED was resistant to IL-1 induced degradation. This result demonstrated that the IκB -ED expressed in HeLa cells was able to be used to monitor endogenous IL-1 receptor activation.

Gq-coupled GPCR Activation in Neuroblastoma Cell Line SK-N-SH

It has been reported that Gq coupled GPCR receptor activation results in NF-KB pathway activation. To demonstrate that the IκB -ED fusion protein can be used as a functional marker to monitor GPCR activation, the neuroblastoma cell line SK-N-SH was used. This cell line was reported to express M3 receptors endogenously. This receptor is Gαq coupled. Carbachol is known as a non-selective agonist to activate M3 receptors. SK-N-SH (ATCC) cells were cultured in MEM medium (Gibco) supplemented with 10% fetal bovine serum and 2 mM glutamine. Cells were seeded into 24 well plates one day before experiment. Then 0.25 µg DNA per well was used to transfect the cells with Fugene6. 24 hr after transfection, cells were treated with carbachol for 20 min at 37° C. Then the cells were lysed and ED activity was assayed as described above. As shown in FIG. 5, carbachol induced M3 activation was indicated by the degradation of IκB-ED, resulting in a decreased RLU reading. The untreated cells were normalized to 100% activity. Upon 30 µM treatment of carbachol, only 50% of the ED activity was retained. The decrease of RLU indicated the induced degradation of IκB -ED fusion protein. The IκB M-ED, on the other hand, did not show the dramatic decrease in activity. More than 92% of ED activity was still retained after treatment with 30 µM carbachol on IκB M-ED expressing cells. This result demonstrated that the ED labeled IκB can also be used to monitor GPCR activation.

M1 Activation Leads to IkB-PL Degradation

CHO-K1 cells stably expressing human M1 muscarinic receptor was obtained from Euroscreen (Belgium). Cells were grown in F-12 medium containing 10% fetal calf serum, penicillin and streptomycin and 400 ug/ml G418. Cells were seeded in 24-well plates one day before transfection. PCMV-IkB-PL was transiently transfected into CHO M1 cells using Fugene6 following manufacturer's protocol. 24 h after transfection, culture medium was replaced and cells were treated with carbachol at a range of different concentrations for 30 min. Culture medium was removed after induction and complementation assay was performed with a chemiluminescent readout (FIG. 14).

MC4 Activation Leads to IkB-PL Degradation

CHO-K1 cells stably expressing human MC4 melanocortin 4 receptor was obtained from Euroscreen. Cells were grown in F-12 medium containing 10% fetal calf serum, penicillin and streptomycin and 400 ug/ml G418. Cells were seeded in 6-well plates one day before transfection. PCMV-IkB-PL was transiently transfected into CHO MC4 cells using Fugene6 following manufacturer's protocol. 24 h after transfection, culture medium was replaced and cells were treated with NDP-α-MSH at indicated concentration for 30 min. Culture medium was removed after induction and complementation assay was performed with a chemiluminescent readout. (FIG. 15).

CCR3 Activation Leads to IkB-PL Degradation

CHO-K1 cells stably expressing human chemokine CCR3 receptor was obtained from Euroscreen. Cells were grown in F-12 medium containing 10% fetal calf serum, penicillin and streptomycin, 5 ug/ml puromycin, 100 ug/ml hygromycin and 400 ug/ml G418. Cells were seeded in 6-well plates one day before transfection. PCMV-IkB-PL was transiently transfected into CHO MC4 cells using Fugene6 following manufacturer's protocol. 24 h after transfection, culture medium was replaced and cells were treated with eotaxin at indicated concentration for 30 min. Culture medium was removed after induction and complementation assay was performed with a chemiluminescent readout. (FIG. 16).

EGFR Activation Leads to IkB-PL Degradation

Hela cells stably expressing IkB-PL were used. To confirm the cells response to EGF, the cell viability assay was performed. Hela-IkB cells were seeded in DMEM with 0.5% FBS in 96 well plate with a density of 5000 cells per well, exposing to a serial dosage of rhEGF. 72 hours later, cell viability assay was performed using the Cell Titer-Glo luminescence Cell Viability assay kit (Promega). Results showed that the viable cell numbers responded to the EGF induction in a dosage dependent manner. (FIG. 17).

To test the response of Hela cells to EGF, Hela cells expressing IkB-PL were seeded in DMEM medium containing 0.5% FBS in 96-well plates with a density of 8000 per well. After incubated at 37C. with 5% CO2 overnight, cells were pre-treated with Cycloheximide (10 ug/ml) for 30 min and then exposed to a serial dosage of rhEGF for 2 hr. The IkB-PL degradation was detected using the DiscoveRx Enzyme Fragment complementation (EFC) Assay. Results demonstrated that IkB degradation upon EGF induction in a dosage dependent manner. (FIG. 18).

Degradation of Nuclear Receptor Labeled with PL (PL-PPAR)

pcDNA3.1-PL-PPAR construct was obtained in the two rounds of the cloning procedure. In the first round, the ED (55-mer) sequence was inserted into NheI and KpnI sites of the pcDNA3.1/zeo vector (Invitrogen). PPARg1 gene was obtained by PCR amplification of the human placenta cDNA library and in the second round of cloning was inserted into KpnI and NotI sites of the vector.

In brief, pcDNA3.1/zeo vector DNA (FIG. 6) was first digested using NheI and KpnI restriction enzymes, then the large fragment was gel purified and ligated to the ED DNA sequence obtained by PCR from existing ED-containing plasmid (pCMV-IkB-ED). ED DNA fragment obtained by PCR was gel purified, digested with the same enzymes and ligated to the purified pcDNA3.1/zeo-NheI-KpnI fragment. The resultant pcDNA3.1-PL construct was used further to create pcDNA3.1-PL-PPARγ1.

PCR amplification of the PPARγ1 coding region was carried out in 100 uL of the reaction mix using 200 uM of 5'- and 3-primers 5' primer: AGACGGTACCATGACCATGGT-TGACACAGAGATG; (SEQ ID NO: 5) 3' primer: GTC-CTCTAGATGTTCCTGAACATGATCCGC-CGGCGCAGA, (SEQ ID NO: 6), 1 uL of human placenta cDNA library (Clontech) and Platinum Taq DNA Polymerase High Fidelity (Invitrogen) according to manufacturer's recommendations. The 1.5 kb PCR product was gel purified using QIAEX II gel extraction kit (Qiagen) and used for the digestion with KpnI and NotI restriction endonucleases. pcDNA3.1-PL construct obtained earlier was digested with the same restriction enzymes (KpnI and NotI), gel purified and ligated to the PPAR KpnI/NotI gene fragment using T4 DNA ligase (Statagene). Ligation mix was used to transform DH5α competent cells and the obtained colonies were mapped by restriction analysis. The presence of the ED-PPARg1 insert in the selected clone was confirmed by DNA sequencing.

Transient Transfection and Detection of PL-PPAR Fusion Protein

The pcDNA3.1-PL-PPAR construct was used to transiently transfect HEK293 cells seeded in 6-well plates. Fugene6 was used as a gene delivery system. Transfections were performed according to manufacturer's instructions. One microgram of plasmid DNA (pcDNA3.1-PL-PPAR) and 3 uL of Fugene6 reagent were mixed together and applied onto 70% confluent monolayer of HEK293 cells. 24-hours after transfection, cells were washed with PBS and then lysed in the lysis buffer (480 uL) containing mild detergent (CHAPS). Total cell lysates were examined for EFC (enzyme fragment complementation of ED and EA) activity or Western blotting. 30 uL of the total cell lysates were placed in 384-well plates in triplicates. 10 uL of EA reagent was added to the wells. After an hour incubation at room temperature 15 uL of the chemiluminescent substrate was added and beta-galactosidase complementation activity was measured within one hour using chemiluminescent reader (Packard). EFC activity negative control was either run as addition of EA dilution buffer added to substitute EA reagent in the control well or cell lysates of the nontransfected cells.

Characterization of PL-PPAR Fusion Protein Using Western Blotting

The expression of PL-PPAR was also confirmed by Western blotting of total cell lysates or immunoprecipitates (FIG. 9). For precipitation, 1 ug of anti-PPAR antibody (Santa Cruz: sc-7196) was immobilized on protein A-sepharose beads in PBS buffer overnight at 4° C. The beads were washed twice with PBS buffer and were incubated with cell lysates for one hour at room temperature. After that the beads were washed four times with PBS buffer and boiled in LDS sample buffer at 100° C. for 5 min. 15 uL of the total cell lysates or immunoprecipitates were then run on NuPage 4-12% Bis-Tris precast polyacrylamide gels and blotted onto nitrocellulose membrane. Membranes were then probed with antibodies to PPARγ (Santa Cruz: sc 7196, sc-7273) followed by secondary antibodies conjugated to alkaline phosphatase. Bands correspondent to endogenous PPARγ(51 kDA) and recombinantly-expressed PL-PPARγ(58 kDA) were visualized using a chromogenic substrate of alkaline phosphatase.

Proteosomal Degradation of Transiently Expressed PL-PPAR

Figure 10A:
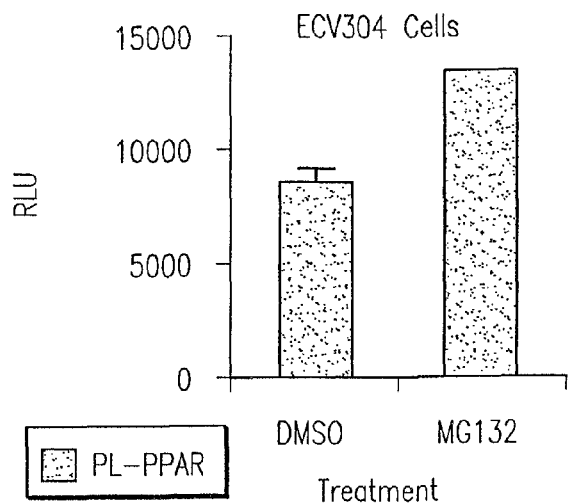
FIG. 10 provides bar graphs showing the enhancement of the amount of PL-PPARγ1 in the presence of MG132 proteosome inhibitor (20 µM). 10A. NIH3T3 cells; 10B. ECV304 cells; and 10C. HeLa cells; indicating basal levels of proteosomal degradation of PL-PPAR.
Figure 10B:
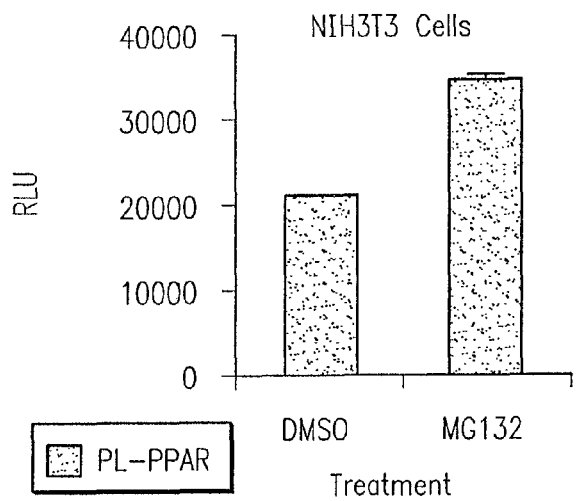
Figure 10C:
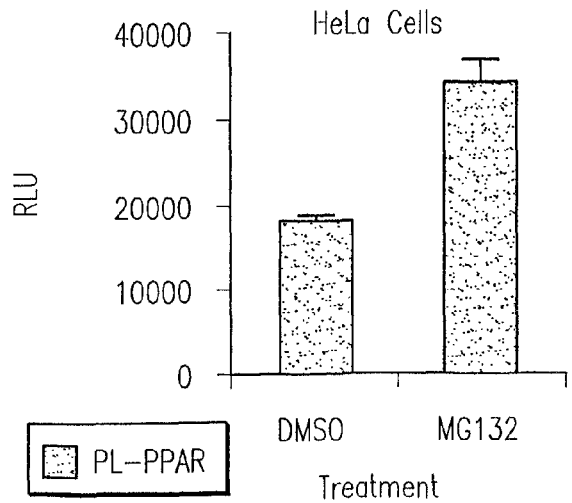

Proteosomal degradation of transiently expressed PL-PPAR protein was detected in NIH3T3, ECV304 and HeLa cells. Cells were transfected with pcDNA3.1-PL-PPAR and 24 hours after transfection medium was removed and cells were treated either with the vehicle (DMSO) or MG132 (proteosome inhibitor). Transfections were carried out in 6-well plates as described above. Cells were washed with PBS buffer, lysed in 480 uL of lysis buffer containing CHAPS (a mild detergent) and tested for ED-EA complementation in triplicates. Thirty microliters of the cell lysates were placed in the wells of 384-well plates. After that, 10 uL of EA solution were added and reaction of complementation was carried out for one hour at room temperature. Fifteen microliters of chemiluminescent substrate (0.4 mM Galacton-Star (Applied Biosystems, Bedford, Mass.) and 2 mg/ml Emerald II substrate (Applied Biosystems, Bedford, Mass.)) were added to the wells and the chemiluminescent signals were read using Chemiluminescent reader (Packard LumiCount, Packard Biosystems) (FIGS. 10A, 10B and 10C).

MG132 Dose-Dependent Increase of PL-PPARγ1

Figure 11:
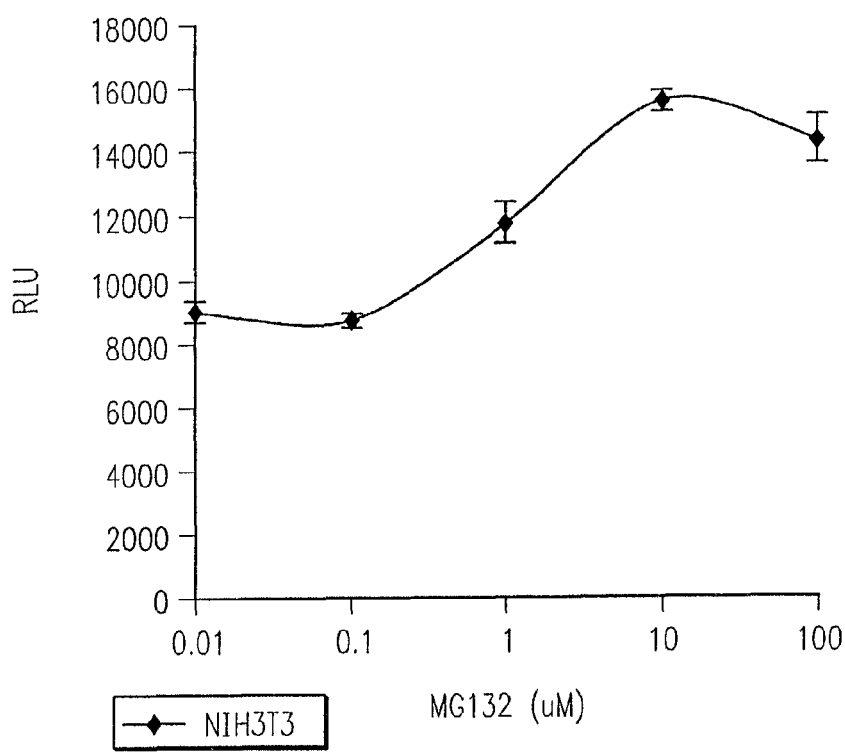
FIG. 11 is a graph showing dose dependent increase in the amount of PL-PPAR protein in the presence of a proteosome inhibitor.

PL-PPAR expression levels were tested in the presence of increasing concentrations of MG132 (FIG. 11). The experiment was done as described above, except that indicated concentrations of MG132 were employed.

Basal Degradation of PL-PPARγ1

Figure 12:
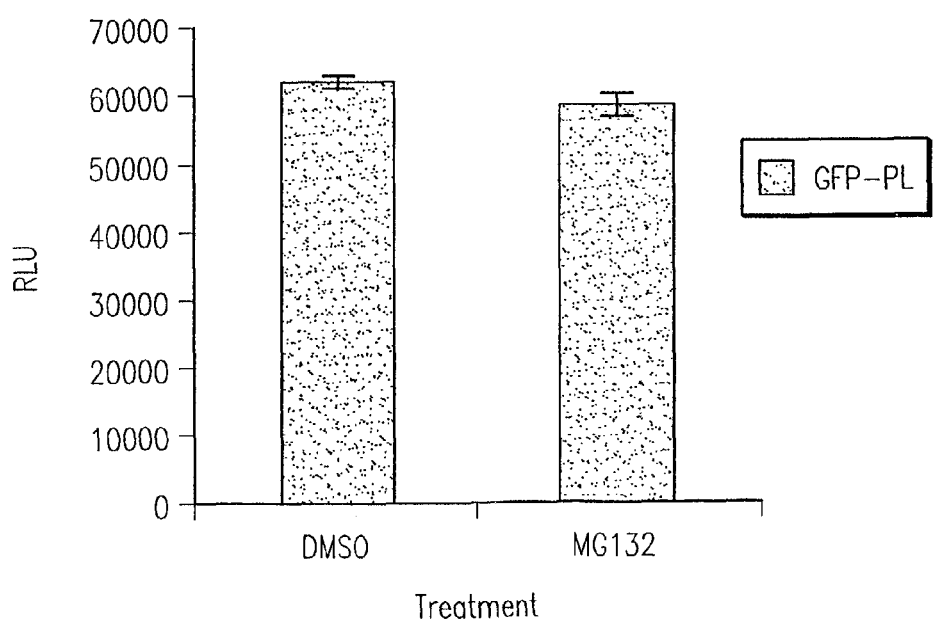
FIG. 12 has bar graphs for DMSO and MG132 showing the effect of a proteosome inhibitor on the lifetime of the fusion protein GEP (green fluorescent protein) -PL

Although, degradation of PPARγ1 protein has been documented in several publications, we investigated whether if in these experiments the attachment of the PL tag triggered degradation. (For publications, see for example, Floyd, et al., 2002 J. Biol. Chem., 277, 4062-8; Waite, et al., 2001 ibid, 276, 7062-8; Hauser, et al., 2000 ibid, 275, 18257-33; Dennis, et al., 2001 Front. Biosci., 6, D954-9 and Wijayaratne and McDonnell 2001 J. Biol. Chem., 276, 35684-92.) We tested GFP protein fused to ED (GFP-PL), a long-lived protein. Unlike PL-PPAR the GFP-PL did not show any degradation (FIG. 12) demonstrating that PL-PPAR degradation was a specific feature of PPAR protein.

Detection of Nuclear Receptor Labeled with PL (PL-PPAR) in the Nucleus of Mammalian Cells The PL-PPAR construct and transfection were performed as described above. The cells were then used to detect localization of the PL-PPAR protein in the cell.

Nuclear localization of PL-PPAR protein was detected 24-hours after transfection of pcDNA3.1-PL-PPAR construct in NIH3T3 or ECV304 cells followed by 2 hr treatment either with DMSO as a vehicle control or 10 uM ciglitazone (CTZ)-PPARγ selective agonist. Transfections were carried out in 6-well plates as described above. Cells were washed with PBS buffer, fixed with 3.7% formaldehyde/PBS solution for 20 min and then permeabilized with 0.1% Tween-20. Cells were further incubated with 500 uL of EA reagent for one hour at room temperature. After the removal of EA reagent the X-Gal staining solution (Invitrogen) was added and plates were incubated at 37° C. at 5% $CO_2$ for 2 hours. Images were visualized and captured using Zeiss HBO 100 microscope (FIGS. 13A and 13B).

The modified cells can be used for a number of purposes. The cells can be used for measuring NF-βB pathway activation, where the cells can be seeded in microtiter plates, treated with a candidate compound, incubated at 37° C. for 30 min and then lysed. After addition of EA and substrate, the generated signal will indicate the effect of the candidate compound on the NF-βB pathway. A signal decrease would indicate that the candidate compound stimulates the pathway. Candidate compounds can be screened for their effect on receptor-ligand interaction, where the receptor-ligand interaction naturally leads to NF-βB pathway activation. The receptor can be co-expressed with the I βB-ED fusion protein in cells or the I βB-ED fusion protein construct can be expressed in cells that express the receptor. The cells are treated with the candidate compounds before addition of the ligand. Inhibition of I βB-ED degradation indicates the inhibition of the receptor activation. Receptors may include those GCPRs, that is, receptors complexed with GTPases, orphan receptors, or any receptor that is coupled to the NF-βB pathway. The protocols can also be used in screening for genes related to the NF-βB pathway. A cDNA expression library can be transfected into cells expressing I βB-ED and any changes in I βB-ED degradation determined. A change in the level of degradation indicates that the gene affects the NF-βB pathway. In this way one can assay for gene function, drug target validation and determining new drug targets. In addition, one may analyze for IKK kinase or ubiquitin pathway activation or inhibition.

By preparing genes for cyclin-ED fusion proteins and transfecting cells with the constructs, one can monitor the cyclin changes as an indicator of cell growth and the effect of candidate compounds on the cyclin, e.g. compounds that control abnormal growth, such as with cancer cells. ED can be fused to p53 and the fusion protein level observed with cell apoptosis, p53 gene modification and p53 accumulation or diminution in the cells.

By having factors that are translocated to the nucleus upon a change in environment, one can determine the transport of the protein to the nucleus. In this way one can measure activators and inhibitors of such translocation. Also, where proteins become associated with large assemblages of proteins to provide a function, e.g. proteasomes, spliceosomes, etc., the reduction in activity of the ED fusion protein can be monitored by the reduction in activity of the ED fusion protein.

It is evident from the above results that the subject invention provides a powerful tool for investigating cellular function, effects of agents on cellular function, identification of targets in cells, identification of interactions between cell components, screening of drug candidates, effects of changes in cellular status, such as differentiation, neoplasia, mitosis, meiosis, etc., on the cellular pathways, and the like. The method is straightforward using available components. The system is provided in a convenient form, where the user can introduce the desired gene of interest into a preformed vector and have the gene in reading frame with the ED (or PL). The fusion proteins are readily prepared and where degradation is involved, the ED (or PL) can be joined at either end. The fusion proteins are biologically active and can serve as surrogates for the natural gene in a negative or positive background. In addition, cells can be provided that are specifically modified for interaction with the construct for the fusion protein, providing for controlled transcription, e.g. inducible, expression or overexpression of particular proteins that can influence the activity of the fusion protein, and the like. Other applications for the subject invention are also available, in monitoring idiosyncratic responses to drugs, response to treatments, changes in cells, etc.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining a change in degradation of a cellular protein in a cellular pathway in response to a candidate compound, said method employing a fragment of from 37 to 110 amino acids of β-galactosidase as an enzyme donor ("ED") and a larger fragment of said β-galactosidase as an enzyme acceptor ("EA"), wherein the two fragments are characterized by complexing to form an active enzyme, further said method employing a mammalian cell into which is introduced a genetic expression construct encoding a surrogate fusion protein comprising said ED and a surrogate for said cellular protein, said method comprising:

expressing said fusion protein in said cell in the presence of said candidate compound, which fusion protein serves as a surrogate for said cellular protein in response to said candidate compound;

lysing said cell to form a lysate;

providing to said lysate a purified EA and a substrate for the ED/EA active complex wherein the complex converts the substrate into a detectable product; and measuring the level of said detectable product produced by the method with the cell in the presence of said candidate compound in comparison to the level of said detectable product produced by the method with a cell in the absence of said candidate compound, wherein a decrease in level of said detectable product in the presence of said candidate compound in comparison to the level of said detectable product in the absence of said candidate compound is indicative of said degradation of said cellular protein in response to said candidate compound.

2. The method according to claim 1, wherein said ED comprises from 37 to 90 amino acids of β-galactosidase.

3. The method according to claim 1, wherein said ED is at a terminus of said surrogate for said cellular protein.

4. The method according to claim 1 wherein said candidate compound is a ligand for a membrane receptor.

5. The method according to claim 1, wherein said fusion protein is expressed transiently.

6. The method according to claim 1, wherein said intracellular protein is IκB.

7. A method for determining a change in translocation to the nucleus of a cellular protein in a cellular pathway in response to a candidate compound, said method employing a fragment of from 37 to 110 amino acids of β-galactosidase as an enzyme donor ("ED") and a larger fragment of said β-galactosidase as an enzyme acceptor ("EA"), wherein the two fragments are characterized by complexing to form an active enzyme, further said method employing a mammalian cell into which is introduced a genetic expression construct encoding a surrogate fusion protein comprising said ED and a surrrogate for said cellular protein, said method comprising:

expressing said fusion protein in said cell in the presence of said candidate compound, which fusion protein serves as a surrogate for said cellular protein in response to said candidate compound;

fixing said cell;

adding EA to the fixed cell and a substrate for the ED/EA active complex wherein the complex converts the substrate into detectable product; and measuring the level of said detectable product in the cell nucleus produced by the method with the cell in the presence of said candidate compound in comparison to the level of said detectable product produced by the method with a cell in the absence of said candidate compound, wherein a change in level of said detectable product in the cell nucleus in the presence of said candidate compound in comparison to said detectable product in the cell nucleus in the absence of said candidate compound is indicative of the change in translocation of said cellular protein in response to said candidate compound.

8. The method according to claim 7, wherein said ED is at a terminus of said surrogate for said cellular protein.

9. The method according to claim 7 wherein said candidate compound is a small organic molecule.

10. The method according to claim 7, wherein said fusion protein is expressed transiently.

* * * * *